US007235520B2

(12) United States Patent
Green et al.

(10) Patent No.: US 7,235,520 B2
(45) Date of Patent: Jun. 26, 2007

(54) METHOD OF INDUCING APOPTOSIS IN LYMPHOID CELLS

(75) Inventors: Michael R. Green, Boylston, MA (US); Laxminarayana Devireddy, Worcester, MA (US); Jose G. Teodoro, Worcester, MA (US); Fabian Richard, Worcester, MA (US)

(73) Assignee: University of Massachusetts, Boston, MA (US)

( * ) Notice: Subject to any disclaimer, the term of this patent is extended or adjusted under 35 U.S.C. 154(b) by 105 days.

(21) Appl. No.: 09/957,801

(22) Filed: Sep. 21, 2001

(65) Prior Publication Data

US 2002/0128194 A1 Sep. 12, 2002

Related U.S. Application Data

(60) Provisional application No. 60/234,216, filed on Sep. 21, 2000.

(51) Int. Cl.
*A61K 38/00* (2006.01)
(52) U.S. Cl. .......................................................... 514/2
(58) Field of Classification Search .................. 512/2; 424/85.1; 530/351
See application file for complete search history.

(56) References Cited

OTHER PUBLICATIONS

Court et al., Biochem Biophys Res Commun. Jun. 18, 2004;319(1):130-7, abstract only.*
Riott et al., (Immunology, Fourth Edition, 1996, Mosby, Chapter 10 only, pp. 10.1-10.15).*
Freshney (Culture of Animal Cells, A Manual of Basic Technique, Alan R. Liss, Inc., 1983, New York, p. 4).*
Dermer (Bio/Technology, 1994, 12:320).*
Devireddy et al., (Aug. 3, 2001, vol. 293, pp. 829-834).*
Persengiev et al., (Jul. 15, 2002, Genes and Development, vol. 16, pp. 1806-1814).*
Kamezaki et al., (Dec. 2003, European Journal of Haematology, vol. 71, pp. p412-p417).*
Lagneaux et al., Blood, vol. 91 No. 7 (Apr. 1, 1998): pp. 2387-2396.*
Gura (Science, 1997, 278:1041-1042).*
Johnson et al., (Brit. J. Cancer 84(10):1424-1431).*
Johnson et al., (Brit. J. Cancer 84(10):1424-1431), May 2001.*
Bowie et al (Science, 1990, 247:1306-1310).*
Burgess et al (J of Cell Bio. 111:2129-2138, 1990).*
Lazar et al (Molecular and Cellular Biology, 1988, 8:1247-1252).*
Bartsch et al., "Cloning and expression of human neutrophil lipocalin cDNA derived from bone marrow and ovarian cancer cells" *FEBS Letters* 357:255-259 (1995).
Boise et al., "*bcl-x*, a *bcl-2*-Related Gene That Functions as a Dominant Regulator of Apoptotic Cell Death" *Cell* 74:597-608 (1993).
Borregaard et al., "Biosynthesis of Granule Proteins in Normal Human Bone Marrow Cells. Gelatinase is a Marker of Terminal Neutrophil Differentation" *Blood-Journal of the American Society of Hematology* 85:812-817 (1995).
Bundgaard et al., "Molecular Cloning and Expression of a cDNA Encoding NGAL: A Lipocalin Expressed in Human Neutrophlis" *Biochemicak and Biophysical Research Communications* 202(3):1468-1475 (1994).
Chu et al., "Demonstration of a glycoprotein derived from 24p3 gene in mouse uterine luminal fluid" *Biochemical Journal* 316:545-550 (1996).
Cowland et al., "Molecular Characterization and Pattern of Tissue Expression of the Gene for Neutrophil Gelatinase-Associated Lipocalin from Humans" *Genomics* 45(1):17-23 (1997).
Flower, "The lipocalin protein family: structure and function" *Biochemical Journal* 318:1-14 (1996).
Friedl et al., "Neutrophil gelatinase-associated lipocalin in normal and neoplastic human tissues. Cell type-specific pattern of expression" The Histochemical Journal 31(7):433-441 (1999).
Garay-Rojas et al., "An apparent autocrine mechanism amplifies the dexamethasone- and retinoic acid-induced expression of mouse lipocalin-encoding gene 24p3" *Gene* 170:173-180, (1996).
Greenberger et al., "Demonstration of permanent factor-dependent multipotential (erythroid/neutrophil/basophil) hematopoietic progenitor cell lines" *Proc. Natl. Acad. Sci. USA* 80;2931-2935 (1983).
Kjeldsen et al., "Isolation and Primary Structure of NGAL, a Novel Protein Associated with Human Neutrophil Gelatinase" *The Journal of Biological Chemistry* 268(14):10425-10432 (1993).
Kjeldsen et al., "Characterization of two ELISAs for NGAL, a newly described lipocalin in human neutrophils" *J Immunol Methods.* 198(2):155-164 (1996).
Liu et al., "Identification of a New Acute Phase Protein" *The Journal of Biological Chemistry* 270(38):22565-22570 (1995).
Liu et al., "Uterocalin: A Mouse Acute Phase Protein Expressed in the Uterus Around Birth" *Molecular Reproduction and Development* 46:507-514 (1997).
Meheus et al., "Identification by microsequencing of lipopolysaccharide-induced prot. secreted by mouse macrophages" *J. Immunol.* 151:1535-1547 (1993).
Nielsen et al., "Induction of NGAL syntesis in epithelial cells of human colorectal neoplasia and inflammatory bowel disease" *Gut* 38:414-420 (1996).
Rudd et al., "Glycosylation of Natural Human Neutrophil Gelatinase B and Neutrophil Gelatinase B-Associated Lipocalin" *Biochemistry* 38(42):13937-13959 (1999).

(Continued)

*Primary Examiner*—Misook Yu
(74) *Attorney, Agent, or Firm*—Fish & Richardson P.C.

(57) ABSTRACT

A two-stage, transcriptionally regulated apoptotic program has been discovered. In the first stage, IL-3 withdrawal results in transcriptional activation of the NGAL gene followed by synthesis and secretion of NGAL protein. In the second stage, secreted NGAL protein induces apoptosis in lymphoid cells by an autocrine mechanism. Based on this discovery, the invention provides a method of inducing apoptosis in a lymphoid cell in a mammal, e.g., a human patient. The invention includes administering a therapeutically effective amount of an NGAL polypeptide or NGAL-like polypeptide to a mammal.

10 Claims, 7 Drawing Sheets

OTHER PUBLICATIONS

Strong et al, "Expression, purification, crystallization and crystallographic characterization of dimeric and monomeric human neutrophil gelatinase associated lipocalin (NGAL)" *Acta Crystallogr D Biol Crystallogr.* 54(Pt 1):93-95 (1998).

Treibel et al., "A 25kDa alpha 2-microglobulin-related protein is a component of the form of human gelatinase" *FEBS LETT.* 314:386-388 (1992).

Wyllie, "Glucocorticoid-induced thymocyte apoptosis is associated with endogenous endonuclease activation" *Nature* 284:555-556 (1980).

Zerega et al., "Expression of NRL/NGAL (neu-related lipocalin/neutrophil gelatinase-associated lipocalin) during mammalian embryonic development and in inflammation" *Eur J Cell Biol.* 79(3):165-172 (2000).

Bundgaard et al. Molecular Cloning and Expression of cDNA Encoding NGAL: A Lipocalin Expressed in Human Neutrophils. *Biochemical and Biophysical Research Communications* 202,3:1468-1475 (1994).

Cowland et al. "Molecular Characterization and Pattern of Tissue Expression of the Gene for Neutrophil Gelatinase-Associated Lipocalin from Humans" *Genomics* 45:17-23 (1997).

Friedl et al. "Neutrophil Gelantinase-Associated Lipocalin in Normal and Neoplastic Human Tissue. Cell Type-Specific Pattern of Expression" *Histochemical Journal* 31:433-441 (1999).

Nielsen et al. "Induction of NGAL Synthesis in Epithelial Cells of Human Colorectal Neoplasia and Inflammatory Bowel Diseases" *Gut* 38,3:414-420 (1996).

Garay-Rojas et al., "An apparent autocrine mechanism amplifies the dexamethasone- and retinoic acid-induced expression of mouse lipocalin-encoding gene 24p3," *Gene*, 170(2):173-180 (1996).

Jiang et al., "Autocrine production and action of IL-3 and granulocyte colony-stimulating factor in chronic myeloid leukemia," *Proc. Natl. Acad. Sci. U.S.A.*, 96(22):12804-12809 (1999).

Karnauskas et al., "Bcl-x(L) and Akt cooperate to promote leukemogenesis in vivo," *Oncogene*, 22(5):688-698 (2003) (abstract only).

Sohur et al., "Rel/NF-kappaB represses bcl-2 transcription in pro-B lymphocytes," *Gene Expr.*, 8(4):219-229 (1999) (abstract only).

Tong et al., "Increased expression of the lipocalin 24p3 as an apoptotic mechanism for MK886," *Biochem. J.*, 372:203-210 (2003).

\* cited by examiner

FIG. 9

```
                       SEQ. ID NO: 5
                    ┌─► SEQ. ID NO: 6
NGAL_Human   1  MPLGLLWLGLALLGALHAQAQDSTSDLIPAPPLSKVPLQQNFQDNQFQGK
NGAL_Mouse   1  MALSVMCLGLALLGVLQSQAQDSTQNLIPAPSLLTVPLQPDFRSDQFRGR
NGAl_Rat     1  MGLGVLCLALVLLGVLQRQAQDSTQNLIPAPPLISVPLQPGSWTERFQGR
                     └─► SEQ. ID NO: 7
NGAL_Human  51  WYVVGLAGNAILREDKDPQKMYATIYELKEDKSYNVTSVLFRKK--KCDY
NGAL_Mouse  51  WYVVGLAGNAVQKKTEGSFTMYSTIYELQENNSYNVTSILVRDQDQGCRY
NGAl_Rat    51  WFVVGLAANAVQKBRQSRFTMYSTIYELQEDNSYNVTSILVRGQ--GCRY NGAL_Human  99  WIRTFVPGCQPGEFTLGNIKSYPGLTSYLVRVVSTNYNQHAMVFFKKVSQ
NGAL_Mouse 101  WIRTFVPSSRAGQFTLGNMHRYPQVQSYNVQVATTDYNQFAMVFFRKTSE
NGAl_Rat    99  WIRTFVPSSRPGQFTLGNIHSYPQIQSYDVQVADTDYDQFAMVFFQKTSE NGAL_Human 149  NREYFKITLYGRTKELTSELKENFIRFSKSLGLPENHIVFPVPIDQCIDG SEQ ID NO:1
NGAL_Mouse 151  NKQYFKITLYGRTKELSPELKERFTRFAKSLGLKDDNIIFSVPTDQCIDN SEQ ID NO:2
NGAl_Rat   149  NKQYFKVTLYGRTKGLSDELKERFVSFAKSLGLKDNNIVFSVPTDQCIDN SEQ ID NO:3
```

FIG. 10

```
NGAL       1 MPLGLLWLGLALLGALHAQAQDSTSDLIPAPPLSKVPLQQNFQDNQFQGKWYVVGLAGNA
24p3       1 MALSVMCLGLALLGVLQSQAQDSTQNLIPAPSLLTVPLQPDRSDQFRGRWYVVGLAGNA
Consensus  1 M L ll LGLALLG L QAQDST  LIPAP L VPLQ  F   QF GkWYVVGLAGNA NGAL      61 ILREDKDPQKMYATIYELKEDKSYNVTSVLFRKKK--CDYWIRTFVPGCQPGEFTLGNIK
24p3      61 VQKKTEGSFTMYSTIYELQENNSYNVTSILVRDQDQGCRYWIRTFVPSSRACQFTLGNMH
Consensus 61 i r        MY TIYEL E  SYNVTSvL R    qgC YWIRTFVP      G FTLGNik NGAL     119 SYPGLTSYLVRVVSTNYNQHAMVFFKKVSQNREYFKITLYGRTKELTSELKENFIRFSKS
24p3     121 RYPQVQSYNVQVALTDYNQFAMVFFRKTSENKQYFKITLYGRTKELSPELKERFTRFAKS
consensus 121  YP  l SY V V sT YNQ AMVFFkK S N+ YFKITLYGRTKELt ELKE F RF KS NGAL     179 LGLPENHIVFPVPIDQCIDG   SEQ ID NO:1
24p3     181 LGLKDDNIIFSVPTDQCIDN   SEQ ID NO:2
Consensus 181 LGL e  IvF VP DQCID    SEQ ID NO:4
```

METHOD OF INDUCING APOPTOSIS IN LYMPHOID CELLS

CROSS-REFERENCE TO RELATED APPLICATIONS

This application claims priority to provisional U.S. application Ser. No. 60/234,216, filed on Sep. 21, 2000, which is herein incorporated by reference in its entirety.

TECHNICAL FIELD

This invention relates to molecular biology, cell biology immunology and oncology.

BACKGROUND

Apoptosis is a physiological form of cell death that plays a role in various biological processes, including normal development, tissue homeostasis, and defense against pathogens (Thompson et al., 1995, *Science* 267:1456-1462). Different forms of apoptosis can be distinguished according to whether transcription and translation, i.e., gene expression, are involved. For example, Fas ligand (FasL) and tumor necrosis factor (TNF) promote cell death by recruiting and activating caspases at the plasma membrane in the absence of transcription and translation (Rathmell et al., 1999, *Annu. Rev. Immunol.* 17:781-828). In contrast, other apoptotic programs require gene expression. The p53 tumor suppressor induces apoptosis in response to genotoxic agents, resulting, at least in part, from transcriptional activation of p53-dependent genes (Polyak et al., 1997, *Nature* 389:300-305). Other transcription-dependent apoptosis programs include glucocorticoid-induced killing of thymocytes (Cohen et al., 1984, *J. Immunol.* 132:38-42) and cell death induced by signaling through the T-cell receptor (TCR) (Lenardo et al., 1999, *Annu. Rev. Immunol.* 17:221-253).

In some cells, apoptosis can be induced by deprivation of trophic factors. For example, transcription-dependent cell death occurs following withdrawal of nerve growth factor (NGF) (Martin et al., 1988, *J. Cell Biol.* 106:829-844). IL-3-dependent cell lines undergo apoptosis upon cytokine withdrawal, and IL-3 promotes survival of several lymphoid progenitors (Palacios et al., 1987, *J. Exp. Med.* 166:12-32; Palacios et al., 1985, *Cell* 41:727-734).

Neutrophil gelatinase associated lipocalin (NGAL), a member of the lipocalin family of proteins, is a secreted 25 kDa glycoprotein found in granules of human neutrophils (Kjeldsen et al., 1993, *J. Biol. Chem.* 268:10425-10432). Lipocalins have been characterized by their ability to bind small lipophilic substances. Lipocalins share a common three-dimensional β-barrel structure which functions, in at least some lipocalins, in binding a lipophilic ligand, e.g., a steroid, bilin, retinoid, or other lipid. For a review of structure and function in the lipocalin family, see Flower, 1996, *Biochem. J.* 318:1-14. Murine forms of NGAL (homologs) from mice and rats are known. NGAL in mice is known by various designations, including NGAL, 24p3 protein, SIP24, P25, lipocalin 2, and uterocalin. NGAL in rats is known as NGAL or alpha 2-microglobulin. NGAL increases 7- to 10-fold in cultured mouse kidney cells in response to viral infection (Hraba-Renevey et al., 1989, *Oncogene* 4:601-608). NGAL is a major secretory product of lipopolysaccharide-stimulated, cultured mouse macrophages (Meheus et al., 1993, *J. Immunol.* 151:1535-1547).

NGAL is a positive acute phase protein. It has been suggested that NGAL is a scavenger of bacterial products at sites of inflammation (Nielsen et al., 1996, *Gut* 38:414-420). It has also been suggested that NGAL has an immunomodulatory function involving the binding of lipophilic inflammatory mediators (Bundgaard et al., 1994, *Biochem. Biophys. Res. Commun.* 202:1468-1475). NGAL is synthesized constitutively at a particular developmental point during the maturation of granulocyte precursors in the bone marrow (Borregaard et al., 1995, *Blood* 85:812-817). In addition, NGAL synthesis can be induced in epithelial cells under certain conditions such as inflammation and malignancy (Neilsen et al., supra; Bartsch et al., 1995, *FEBS Lett.* 357:255-259; Bundgaard et al., supra).

A full-length cDNA encoding human NGAL protein has been cloned and sequenced (Bundgaard et al., supra). In addition, the human NGAL gene, which includes seven exons and six introns, has been cloned and sequenced, and its expression in various tissues has been analyzed (Cowland et al., 1997, *Genomics* 45:17-23). The human NGAL gene encodes a polypeptide of 197 amino acids, with a 19- or 20-amino acid signal sequence, and a mature NGAL polypeptide containing 178 amino acids (Bundgaard, supra). The motifs Gly-X-Trp (amino acids 48-50 in mature human NGAL) and Thr-Asp/Asn-Tyr (amino acids 132-134 in mature human NGAL) are present in all known lipocalins (Bundgaard et al., supra). On the basis of X-ray crystallography, it has been suggested that these motifs are important in the tertiary structure common to lipocalins, i.e., an eight-stranded antiparallel β-barrel surrounding a hydrophobic core (Cowan et al., 1990, *Proteins: Structure Function and Genetics* 8:44-61). The cysteine residues 95 and 194 in the human NGAL sequence are conserved, and have been reported to form an intramolecular disulfide bridge (Bundgaard, supra; Cowan et al., 1990, supra). Human NGAL contains a single N-glycosylation site (an asparagine residue) at position 65 of the mature amino acid sequence (approximately position 84 or 85 of the pre-NGAL polypeptide).

SUMMARY

A two-stage, transcriptionally regulated apoptotic pathway has been discovered. In the first stage, IL-3 withdrawal results in transcriptional activation of the NGAL gene followed by synthesis and secretion of NGAL protein. In the second stage, secreted NGAL protein induces apoptosis in lymphoid cells by an autocrine mechanism.

On the basis of this discovery, the invention provides a method of inducing apoptosis in a lymphoid cell. The cell can be from a mammal, e.g., a human. The method includes administering an amount of an NGAL polypeptide or NGAL-like polypeptide effective to ameliorate a symptom of a lymphoid disease, e.g., a leukemia or autoimmune disorder. In some embodiments, the polypeptide contains an amino acid sequence having at least 80% sequence identity with amino acid 21 to C-terminal amino acid of the human, mouse, or rat NGAL amino acid sequence in FIG. 9 (SEQ ID NOS:5, 6, and 7, respectively). In some embodiments, the polypeptide contains an amino acid sequence containing amino acid 21 to the C-terminal amino acid of the human, mouse or rat NGAL amino acid sequence in FIG. 9 (SEQ ID NOS:5, 6, and 7, respectively) with up to 30 conservative amino acid substitutions, and up to 20 amino acid deletions or non-conservative amino acid substitutions. In some embodiments, the polypeptide contains a consensus or composite sequence alignable with amino acid 21 to the C-terminal amino acid of the NGAL amino acid alignment in FIG. 9, wherein each position in the consensus or composite sequence contains an amino acid or a gap selected from the corresponding position in the alignment in SEQ ID NOS:1, 2, or 3. Specific examples of mature NGAL polypeptides are amino acid 21 to the C-terminal amino acid of the human NGAL amino acid sequence in FIG. 9 (SEQ ID NO:5); amino acid 21 to the C-terminal amino acid of the mouse NGAL amino acid sequence in FIG. 9 (SEQ ID NO:6); and amino acid 21 to the C-terminal amino acid of the rat NGAL amino acid sequence in FIG. 9 (SEQ ID NO:7).

The lymphoid cell in which apoptosis is induced can be a cell in vivo, for example a T-lymphocyte or a B-lymphocyte, which may or may not be leukemic. The NGAL or NGAL-like polypeptide can be administered parenterally, e.g., intravenously.

The invention also features a method of treating a leukemia in a mammal, e.g., a human. The method includes administering to the mammal an amount of an NGAL polypeptide or NGAL-like polypeptide effective to ameliorate a symptom of the leukemia.

The invention also features a method of treating an immune disorder in a mammal, e.g., a human. The method includes administering an amount of an NGAL polypeptide or NGAL-like polypeptide effective to ameliorate a symptom of the immune disorder. Immune disorders that can be treated with an NGAL polypeptide or NGAL-like polypeptide include autoimmune disorders such as autoimmune lymphproliferative syndrome (ALPS).

As used herein, "NGAL polypeptide" means a glycosylated or nonglycosylated polypeptide whose amino acid sequence is a naturally occurring, mature NGAL amino acid sequence. An NGAL polypeptide can be isolated from a natural source or it can be produced by recombinant DNA methods. Examples of NGAL polypeptides include polypeptides consisting of the amino acid sequences set forth in FIGS. 9 and 10, excluding the N-terminal signal sequences.

As used herein, "NGAL-like polypeptide" means a polypeptide whose amino acid sequence meets at least one of the following criteria:

(a) it contains an amino acid sequence that has at least 80% sequence identity with amino acid 21 to the C-terminal amino acid of the human, mouse, or rat NGAL amino acid sequence set forth in FIG. 9;

(b) it contains an amino acid sequence consisting of amino acid 21 to the C-terminal amino acid of the human, mouse, or rat NGAL amino acid sequence set forth in FIG. 9, with up to 30 conservative amino acid substitutions; and up to 20 amino acid deletions or non-conservative amino acid substitutions (in any combination); or (c) it contains a consensus or composite sequence alignable with amino acid 21 to the C-terminal amino acid of the three-sequence, NGAL amino acid alignment in FIG. 9, wherein each position in the consensus or composite sequence contains an amino acid or a gap selected from the three entries at the corresponding position in the alignment in FIG. 9.

As used herein, "mature NGAL amino acid sequence" means the amino acid sequence of an NGAL gene product after removal of a signal sequence in a eukaryotic cell secretion process.

As used herein, "conservative amino acid substitution" means a substitution within an amino acid family. Families of amino acids are recognized in the art and are based on physical and chemical properties of the amino acid side chains. Families include the following: amino acids with basic side chains (e.g. lysine, arginine, and histidine); amino acids with acidic side chains (e.g., aspartic acid and glutamic acid); amino acids with uncharged polar side chains (e.g. glycine, asparagine, glutamine, serine, threonine, tyrosine, and cysteine); amino acids with nonpolar side chains (e.g. alanine, valine, leucine, isoleucine, proline, phenylalanine, methionine, and tryptophan); amino acids with branched side chains (e.g., threonine, valine, and isoleucine); and amino acids with aromatic side chains (e.g., tyrosine, phenylalanine, tryptophan, and histidine). An amino acid can belong to more than one family.

As used herein, "therapeutically effective" amount or dose refers to that amount of the compound sufficient to result in amelioration of at least one symptom of a disease or disorder, e.g., a leukemia or autoimmune disorder. Such symptoms are known in the art (for example, see Berkow et al., *The Merck Manual*, Merck Research Laboratories, N.J., 1992)

Unless otherwise defined, all technical and scientific terms used herein have the same meaning as commonly understood by one of ordinary skill in the art to which this invention belongs. In case of conflict, the present application, including definitions, will control. All publications, patents, and other references mentioned herein are incorporated by reference in their entirety.

Although methods and materials similar or equivalent to those described herein can be used in the practice or testing of the present invention, useful methods and materials are described below. The materials, methods and examples are illustrative only and not intended to be limiting. Other features and advantages of the invention will be apparent from the detailed description and from the claims.

DESCRIPTION OF DRAWINGS

FIG. 9 is an alignment of complete amino acid sequences of pre-NGAL polypeptides from human (SEQ ID NO:1), mouse (SEQ ID NO:2) and rat (SEQ ID NO:3). SEQ ID NO:5 is human NGAL from amino acid 21 through the COOH terminus. SEQ ID NO:6 is mouse NGAL (24p3) from amino acid 21 through the COOH terminus. SEQ ID NO:7 is rat NGAL from amino acid 21 through the COOH terminus.

FIG. 10 is an alignment of complete amino acid sequences from pre-NGAL polypeptides from mouse (SEQ ID NO:2) and human (SEQ ID NO:1). A mouse/human consensus sequence is shown also (SEQ ID NO:4).

DETAILED DESCRIPTION

Figures 1A, 1B, 1C:
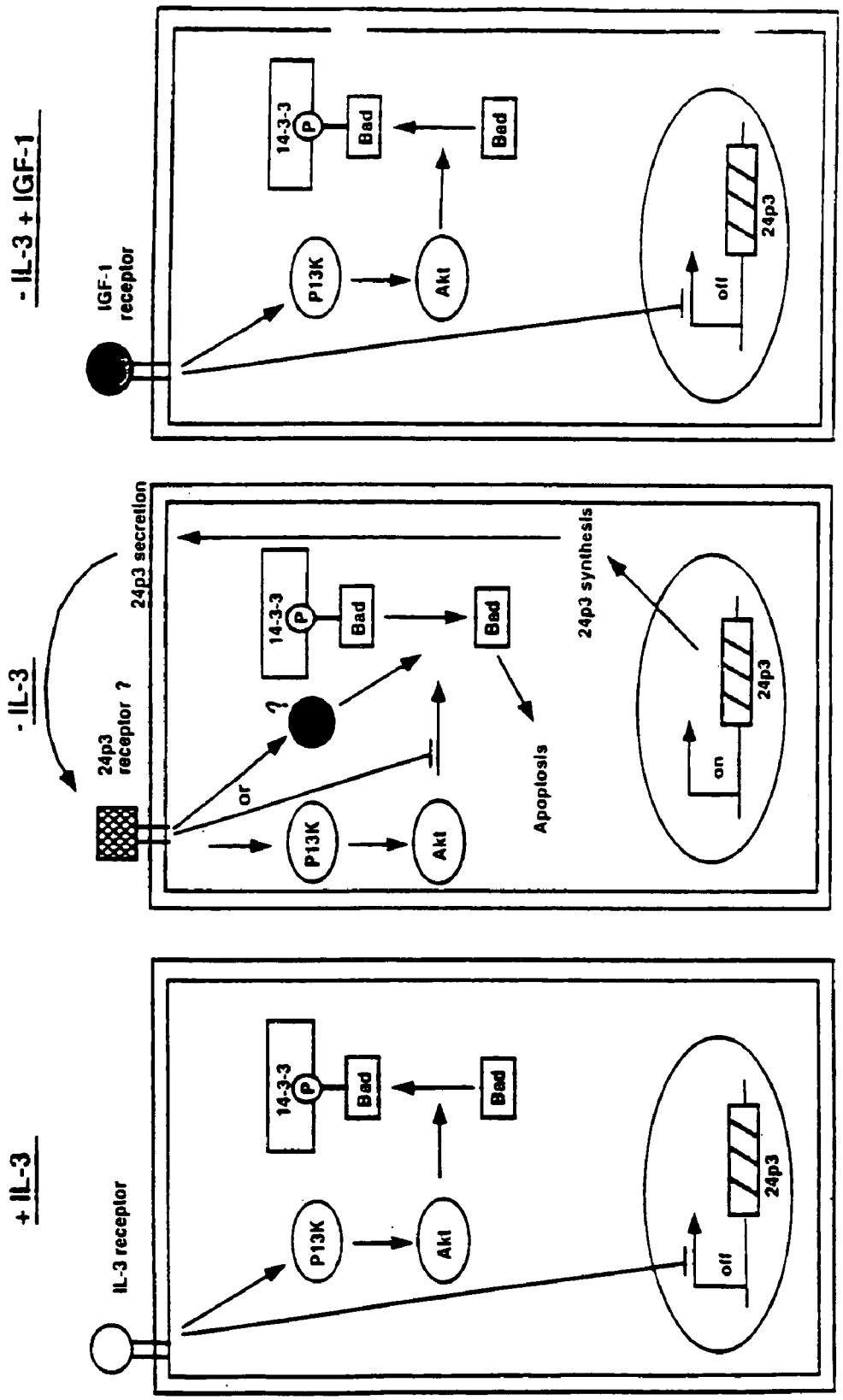
FIGS. 1A-1C are schematic diagrams illustrating the apoptotic pathway by which NGAL induces apoptosis in lymphoid cells.

Experimental results leading to the present invention indicate that a major function of IL-3 in promoting cell viability is to maintain the NGAL (e.g., human NGAL, murine 24p3) gene in a transcriptionally repressed state. IGF-1 can substitute for IL-3 by preventing apoptosis following cytokine deprivation (See Rodriguez-Tarduchy et al., 1992, *J. Immunol.* 149:535-540). The inventors have found that like IL-3, IGF-1 blocks NGAL transcriptional activation, explaining how IGF-1 can prevent apoptosis. When transcriptional repression of the NGAL gene is artificially bypassed by addition of NGAL protein, IL-3 and IGF-1 fail to prevent apoptosis. Thus, the NGAL protein can be used therapeutically to induce apoptosis specifically in lymphoid cells, regardless of the presence of cytokines such as IL-3 and IGF-I. While the inventors do not intend to be bound by theory, a predicted apoptotic pathway is illustrated schematically in FIGS. 1A-1C.

Leukemias are a group of neoplastic diseases of blood-forming organs. Leukemias are characterized by an abnormal increase in the production of leukocytes, including lymphoid cells. Because the invention provides for reducing a lymphoid cell population through induction of apoptosis specifically in lymphoid cells, the invention is useful in treating leukemias and other diseases or disorders, e.g., immune disorders, that are characterized by an abnormally high number of lymphoid cells.

NGAL and NGAL-Like Polypeptides

Preferably, the polypeptide used in methods of the invention includes a mature human NGAL amino acid sequence. For example, a suitable NGAL polypeptide consists of amino acid 21 to the terminal amino acid of the human NGAL amino acid sequence set forth in FIG. 9 or FIG. 10. However, a polypeptide containing any of various NGAL or NGAL-like amino acid sequences can also be used in the invention. For example, those of skill in the art will recognize that within a species, natural amino acid polymorphisms may occur in the NGAL amino acid sequences found in different individuals. Accordingly, the use of various naturally occurring forms of human wild type NGAL polypeptides is within the scope of the invention.

The use of natural NGAL polypeptides (or portions thereof) from various mammalian species to induce apoptosis in lymphoid cells is within the scope of the invention. The currently known natural NGAL sequences, i.e., those from human, mouse, and rat, have highly conserved amino acid sequences (FIG. 9), and cross-species activity in specifically inducing apoptosis in lymphoid cells (but not other cell types). This is demonstrated in the Experimental Examples (below). The invention therefore includes, for example, the use of a mouse or rat NGAL polypeptide in a human patient, or the use of a human NGAL polypeptide in a non-human animal undergoing veterinary treatment. In some embodiments, a chimeric NGAL polypeptide is used, e.g., an artificial NGAL-like polypeptide formed by replacing a portion of a human NGAL amino acid sequence with a corresponding portion of an NGAL amino acid sequence from another species.

A polypeptide containing a consensus (composite) sequence, wherein each amino acid position represents an amino acid or a gap from the alignment in FIG. 9 or FIG. 10, will induce apoptosis in lymphoid cells, and thus be useful in methods of the invention. An NGAL-like polypeptide containing at least 80% sequence identity, e.g., 85%, 90%, 95%, 98% or 99%, with the mature human (SEQ ID NO:5), mouse (SEQ ID NO:6), or rat (SEQ ID NO:7) NGAL amino acid sequence in FIG. 9 will also be useful in methods of the invention. Further, an NGAL-like polypeptide containing amino acid 21 to the C-terminal amino acid of the human (SEQ ID NO:5), mouse (SEQ ID NO:6), or rat NGAL (SEQ ID NO:7) amino acid sequence in FIG. 9, with up to 30, e.g., 1, 3, 5, 10, 15, 20, or 25, conservative amino acid substitutions; and up to 20, e.g., 1, 3, 5, 10 or 15, non-conservative amino acid substitutions or deletions (in any combination, e.g., 10 deletions and 10 substitutions) will be useful in methods of the invention as long as the resulting polypeptide still induces apoptosis in a lymphoid cell. In the preceding sentence, "deletion" refers one amino acid. Thus, "20 deletions" means deletion of a total of 20 amino acid residues, which may or may not be consecutive.

The determination of percent identity between two amino acid sequences is accomplished using the BLAST 2.0 program, which is available to the public on the world wide web at ncbi.nlm.nih.gov/BLAST. Sequence comparison is performed using an ungapped alignment and using the default parameters (Blossom 62 matrix, gap existence cost of 11, per residue gap cost of 1, and a lambda ratio of 0.85). The mathematical algorithm used in BLAST programs is described in Altschul et al., 1997, *Nucleic Acids Research* 25:3389-3402.

In certain embodiments, an NGAL polypeptide or NGAL-like polypeptide used in the invention is glycosylated. For example, the glycosyl moiety is N-linked to an amino acid residue, e.g., an asparagine residue, whose position can be from residue 60 to residue 70, e.g., residue 65, in a mature NGAL polypeptide. See Rudd et al., 1999, *Biochemistry* 38:13937-13950. A glycosylated NGAL polypeptide can be obtained by purification of a naturally occurring NGAL polypeptide from a suitable source, e.g., neutrophils from humans, rabbits, mice, or rats. Recombinant, glycosylated NGAL polypeptides or NGAL-like polypeptides can be produced by conventional methods, using transformed eukaryotic cells, e.g., yeast cells.

In some embodiments of the invention, an NGAL polypeptide or NGAL-like polypeptide is modified by derivatization of amino acid side chains, chemical conjugation, or fusion to non-NGAL peptide moieties. For example an NGAL amino acid sequence can be fused to an N-terminal peptide moiety or C-terminal peptide moiety, to increase in vivo serum half-life of the polypeptide. In some embodiments, the NGAL polypeptide contains one or more modified amino acids, e.g., D-amino acids. Modified amino acids are useful for purposes such as increasing serum half-life of the polypeptide.

Production of NGAL and NGAL-Like Polypeptides

Polypeptides for use in the invention can be obtained by any suitable method. One method of producing an NGAL polypeptide or NGAL-like polypeptide is recombinant production, which involves genetic transformation of a host cell with a recombinant nucleic acid vector encoding the polypeptide or pre-polypeptide, expression of the recombinant nucleic acid in the transformed host cell, and collection and purification of the NGAL or NGAL-like polypeptide. Guidance and information concerning recombinant DNA methods and materials for production of polypeptides can be found in numerous treatises and reference manuals, e.g., Sambrook et al., 1989, *Molecular Cloning—A Laboratory Manual, 2nd Ed.*, Cold Spring Harbor Press; Ausubel et al., (eds.), 1994, *Current Protocols in Molecular Biology*, John Wiley & Sons, Inc.; Innis et al., 1990, *PCR Protocols*, Academic Press. Complete nucleotide sequences are available publicly from GenBank: Accession No. 1171700 (human NGAL); 266619 (rat NGAL); 112725 (mouse NGAL). For specific guidance concerning cloning of human NGAL cDNA by PCR, and recombinant production of human NGAL polypeptides, see Bundgaard et al., 1994, *Biochem. Biophys. Res. Commun.* 202:1468-1475. See also Bartsch et al., 1995, *FEBS Lett.* 357-255-259.

NGAL polypeptides useful in the invention also can be isolated from natural sources. For example human NGAL can be isolated from human neutrophils using methods and materials such as those described in Kjeldsen et al., 1993, *J. Biol. Chem.* 268:10425-10432.

Alternatively, an NGAL polypeptide or NGAL-like polypeptide can be obtained directly by chemical synthesis, e.g., using a commercial peptide synthesizer according to the vendor's instructions. Methods and materials for chemical synthesis of polypeptides are well known in the art.

Techniques for purification of NGAL polypeptides from biological material are known in the art. For specific guidance concerning purification of NGAL polypeptides, see, e.g., Kjeldsen et al., supra. In addition, techniques for production of anti-NGAL antibodies and the use of the antibodies in purification and assay of NGAL polypeptides are known in the art. See, e.g., Kjeldsen et al., supra; Liu et al., 1997, *Molecular Reproduction and Development* 46:507-514.

Effective Dose

Toxicity and therapeutic efficacy of the NGAL polypeptides and NGAL-like polypeptides of the invention can be determined by standard pharmaceutical procedures, using either cells in culture or experimental animals to determine the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Polypeptides that exhibit large therapeutic indices are preferred. While polypeptides that exhibit toxic side effects may be used, care should be taken to design a delivery system that targets such compounds to the site of affected tissue to minimize potential damage to non-target cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the methods of the invention, the therapeutically effective dose can be estimated initially from cell culture assays. A dose can also be calculated in animal models to achieve a circulating plasma concentration range that includes the IC50 (that is, the concentration of the test compound which achieves a half-maximal inhibition of symptoms) as determined in cell culture. Such information can be used to more accurately determine useful doses in humans.

Formulation, Dosage and Administration

An NGAL polypeptide or NGAL-like polypeptide can be administered according to the invention by any suitable method. Preferably, the polypeptide is administered parenterally, to avoid digestion in the stomach. Parenteral administration can be systemic, e.g., by an intravenous route. In some embodiments of the invention, the polypeptide is administered locally, e.g., into a tumor or lymph node.

The present invention provides a pharmaceutical composition for treating an individual in need of treatment for a lymphoid cell disease (e.g., a leukemia or autoimmune disorder). The treatment method entails administering a therapeutically effective amount of an NGAL polypeptide or NGAL-like polypeptide that causes apoptosis of a lymphoid cell and a pharmaceutically acceptable carrier, diluent, excipient, or adjuvant.

The pharmaceutical compositions can be used for humans or animals (e.g., mammals) and will typically include any one or more of a pharmaceutically acceptable diluent, carrier, excipient, or adjuvant. The choice of pharmaceutical carrier, excipient, and diluent can be selected with regard to the intended route of administration and standard pharmaceutical practice. The pharmaceutical compositions can include as (or in addition to) the carrier, excipient, or diluent, any suitable binder(s), lubricant(s), suspending agent(s), coating agent(s), or solubilizing agent(s).

The invention includes pharmaceutical formulations that include a pharmaceutically acceptable excipient and an NGAL polypeptide or NGAL-like polypeptide. Such pharmaceutical formulations can be used in a method of treating a lymphoid cell disease such that at least one symptom of the disease is ameliorated. Such a method entails administering to the organism a therapeutically effective amount of the pharmaceutical formulation, i.e., an amount sufficient to ameliorate signs and/or symptoms of the lymphoid cell disease. In particular, such pharmaceutical formulations can be used to treat lymphoid cell disease in mammals such as humans and domesticated mammals (e.g., cows, pigs, dogs, and cats). The efficacy of such treatment can be estimated in an animal model system well known to those of skill in the art as discussed herein.

Treatment includes administering a pharmaceutically effective amount of a composition containing an NGAL polypeptide or NGAL-like polypeptide to a subject in need of such treatment, thereby ameliorating symptoms of a lymphoid cell disorder in the subject. Such a composition typically contains from about 0.1 to 90% by weight (such as 1 to 20% or 1 to 10%) of an NGAL polypeptide or NGAL-like polypeptide of the invention in a pharmaceutically acceptable carrier.

Injectable formulations of the compositions can contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol, and the like). For intravenous injections, water soluble versions of the compounds can be administered by the drip method, whereby a pharmaceutical formulation containing the NGAL polypeptide or NGAL-like polypeptide and a physiologically acceptable excipient is infused. Physiologically acceptable excipients can include, for example, 5% dextrose, 0.9% saline, Ringer's solution, or other suitable excipients. For intramuscular preparations, a sterile formulation of a suitable soluble salt form of the compounds can be dissolved and administered in a pharmaceutical excipient such as Water-for-Injection, 0.9% saline, or 5% glucose solution. A suitable insoluble form of the compound can be prepared and administered as a suspension in an aqueous base or a pharmaceutically acceptable oil base, such as an ester of a long chain fatty acid, (e.g., ethyl oleate). Oral or topical methods of delivery may be used. Such methods are known in the art.

The optimal percentage of the NGAL polypeptide or NGAL-like polypeptide in each pharmaceutical formulation varies according to the formulation itself and the therapeutic effect desired in the specific pathologies and correlated therapeutic regimens. Appropriate dosages of the NGAL-polypeptide or NGAL-like polypeptide can be determined by those of ordinary skill in the art of medicine by monitoring the mammal for signs of disease amelioration or inhibition, and increasing or decreasing the dosage and/or frequency of treatment as desired. The optimal amount of the NGAL polypeptide or NGAL-like polypeptide used for treatment of lymphoid cell diseases depends upon the manner of administration, the age and the body weight of the subject, and the condition of the subject to be treated. Generally, the NGAL polypeptide or NGAL-like polypeptide is administered at a dosage of 1 to 100 mg/kg body weight, and typically at a dosage of 1 to 10 mg/kg body weight. In treatment of a lymphoid cell disorder such as a leukemia or immune disorder, dosage is adjusted so as to achieve an NGAL polypeptide or NGAL-like polypeptide serum concentration in the range of 0.1 ng/ml to 100 ng/ml, e.g., in the range of 1.0 ng/ml to 20 ng/ml, at least once every two weeks, e.g., once per week, once every third day, once every second day, or once per day. Such optimization is within ordinary skill in the art. The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

Natural NGAL is a secreted protein, and its target in the induction of apoptosis in lymphoid cells is believed to be exposed on the outside of the lymphoid cells, which occur in the blood and lymphatic system. Therefore, in the practice of the invention the NGAL polypeptide or NGAL-like polypeptide need not cross cytoplasmic membranes or otherwise enter into cells, nor does it need to penetrate solid tissues to be effective.

An NGAL polypeptide or NGAL-like polypeptide can be formulated into a pharmaceutical composition by admixture with pharmaceutically acceptable nontoxic excipients or carriers. Such compositions can be prepared for use in parenteral administration, particularly in the form of liquid solutions or suspensions. The composition can be administered conveniently in unit dosage form. Such methods are described, e.g., in *Remington's Pharmaceutical Sciences*, Mack Pub. Co., Easton, Pa. In some embodiments, the polypeptide is administered gradually, in a buffered saline solution, by intravenous infusion.

Animal Models

Animal models can be used for testing NGAL polypeptides and NGAL-like polypeptides, e.g., for their efficacy in treating a disorder, estimating toxicity, and dosages. Methods for performing such tests are known in the art. Suitable animal models include animal models for leukemias and autoimmune disorders, e.g., an Fas knockout mouse which exhibits an autoimmune lymphoproliferative syndrome (APLS).

EXPERIMENTAL EXAMPLES

The invention is further illustrated by the following examples. The examples are provided for illustrative purposes only. They are not to be construed as limiting the scope or content of the invention in any way.

Throughout the examples, the term "24p3" is used to designate the murine form of NGAL found in mice.

Example 1

Experimental Methods

Culture of Cell Lines and Primary Cells

For cell lines, all the culture media were supplemented with 10% heat-inactivated FBS. COS-7, NIH 3T3, HeLa, and WEHI 7.1.C.4 cells were maintained in Dulbecco's modified Eagle's medium (DMEM); U20S cells were cultured in McCoy 5A medium; Jurkat and MT4 cells were maintained in RPMI-1640 medium; and HL-60 cells were maintained in Iscove's modified DMEM. FL5.12, LyD9, Baf/3 and 32D cells were cultured in RPMI-1640 medium supplemented with 0.05 mM 2-mercaptoethanol and 3 ng/ml recombinant IL-3 (Pharmingen). HT-2 cells were cultured in RPMI-1640 medium supplemented with 0.05 mM 2-mercaptoethanol, 4.5 g/L glucose, 10 mM HEPES, 1 mM sodium pyruvate, and 200 IU/ml recombinant IL-2 (Pharmingen). D1-F4 cells were cultured in RPMI-1640 medium supplemented with 0.05 mM 2-mercaptoethanol and 50 ng/ml recombinant IL-7 (PeproTech).

Human monocytes obtained from healthy donors (provided by Dr. Mario Stevenson) were initially cultured in DMEM supplemented with 10% heat-inactivated human serum (Sigma), 2 mM L-glutamine, and 8 ng/ml MCSF (Sigma). After 3 days, MCSF was removed from the culture medium. Primary thymocytes from four week-old mice were cultured in DMEM supplemented with 10% heat-inactivated FBS and 1 mM sodium pyruvate.

Transfections of Cell Lines

For establishment of a 24p3 ecdysone-inducible cell line, the 24p3 cDNA containing a hemagglutinin (HA) tag at the C-terminus was cloned into the ecdysone-inducible vector, pIND (Invitrogen). FL5.12 cells were transfected with Superfect (Qiagen) according to the manufacturer's instructions. FL5.12 cells were first transfected with pVGRXR expressing the subunits of the ecdysone receptor and selected with 600 µg/ml Zeocin (Invitrogen) and the resulting clones were then transfected with pIND/24p3-HA and selected with 800 µg/ml G418 (GIBCO-BRL). 24p3 expression was induced by addition of 10 µM ponasterone A (Invitrogen).

For construction of a stable cell line expressing 24p3, the 24p3 cDNA was PCR amplified and cloned into the EcoRI and BamHI sites of pcDNA3 vector (Invitrogen). COS7 cells were transfected with pcDNA3/24p3 and selected with G418 at 600 µg/ml. G418 resistant colonies were isolated and screened for 24p3 expression by Northern blotting and immunoblotting.

Measurements of Apoptosis

IL-3 withdrawal and cell viability determinations were performed as described in Boise et al., 1993, *Cell* 74 597-608. For cell death assays $2 \times 10^5$ cells (lymphoid) or $8 \times 10^5$ cells (fibroblast) in a 60 mm dish were incubated with culture medium from IL-3 deprived FL5.12 cells or COS-7 cells transfected with pcDNA3 or pcDNA3/24p3, supplemented with 3 ng/ml IL-3. For fibroblasts both floating and adherent cells (after trypsinization) were collected at the indicated time points and analyzed by a trypan blue (Sigma) dye exclusion assay. A minimum of 400 cells was counted and all experiments were performed in duplicate. Apoptosis was also assessed by staining with Annexin V-FITC and propidium iodide (Calbiochem) according to the manufacturer's instructions. Stained cells were analyzed in Beckton Dickinson flow cytometer.

For DNA fragmentation analysis, DNA from $2 \times 10^6$ cells was isolated by phenol extraction and analyzed on a 1% agarose gel as described in Rodriguez-Tarduchy et al., 1990, *EMBO J.* 9:2997-3002.

Transcription Profiling using DNA Microarrays

FL5.12 cells were cultured and subjected to IL-3 deprivation as described (see Boise, 1993, *Cell* 74:597-608). Poly(A)+mRNA was isolated eight hours following IL-3 withdrawal using an Oligotex Direct mRNA isolation kit from Qiagen. A cDNA library was generated using Superscript choice system from GIBCO-BRL following the manufacturer's instructions. The cDNA library was transcribed in vitro with biotinylated nucleotides (T7 Megascript kit from Ambion) and the resulting cRNA was used to probe Affymetrix oligonucleotide arrays representing 30,000 known genes or ESTs.

Northern Blot and Immunoblot Analysis

For Northern blotting, 2 µg of poly(A)+RNA or 10 µg of total RNA was analyzed on denaturing formaldehyde agarose gels (See Ausubel et al., *Current Protocols in Molecular Biology*, New York: John Wiley & Sons, Inc., 1992). The blots were probed with the indicated probes and washed under high stringency conditions.

For detection of 24p3 in culture medium, 2 ml of culture medium of cells grown in the presence or absence of IL-3 was concentrated in Centricon YM-10 filters (Millipore) and the retentates were collected and analyzed on a 12% SDS-PAGE gel. The membrane was incubated with 24p3 antibody (see Chu et al., 1996, *Biochem. J.* 316:545-550) and developed with an ECL kit from Amersham.

For analysis of Bad phosphorylation, FL5.12 cells were treated with culture medium from Cos-7 cells transfected with pcDNA3 or the 24p3 expression vector. Cells were lysed in 1% NP-40 lysis buffer containing 20 mM Tris-HCl, pH 7.4, 150 mM NaCl, 1.5 mM $MgCl_2$, 1 mM EDTA, 10 mM NaF, 0.2 mM $Na_3VO_4$, 1 mM $Na_3MoO_4$, and protease inhibitor tablets from Boehringer-Mannheim. Cell lysates were incubated with 2 µg of Bad antibody (Transduction labs). Immune-complexes were resolved by 12% SDS-PAGE and transferred onto a PVDF membrane (Millipore). Blots were incubated with either a phospho-specific Bad antibody (New England Biolabs) or Bad antibody and developed with ECL kit from Amersham.

Example 2

Transcriptional Activation Following IL-3 Deprivation

To identify genes that are activated by IL-3 withdrawal, transcription profiling using high-density DNA microarrays was performed. The mouse pro-B lymphocytic cell line FL5.12 was used because it is dependent on IL-3 for growth and undergoes apoptosis in the absence of cytokine (Boise et al., 1993, *Cell* 74:597-608), which is first detectable approximately six hours following IL-3 deprivation (See McCubrey et al., 1989, *Oncogene Res.* 4, 97-109). FL5.12 poly(A)+mRNA was isolated eight hours after IL-3 withdrawal and used to interrogate Affymetrix DNA microarrays representing approximately 30,000 genes. Transcription profiles of cells grown in the presence or absence of IL-3 were compared. The genes for which the most significant transcriptional changes occurred following IL-3 withdrawal are listed in Table 1. The gene that underwent the largest transcriptional activation was 24p3, which encodes a member of the lipocalin family. A lower but substantial level of activation was also observed for several other genes, including mNip3 (See Chen et al., 1999, *Biol. Chem.* 274:7-10) and p40Phox (see Endres et al., 1997, *Immunity* 7: 419-432). Conversely, transcription of several genes decreased following IL-3 withdrawal, the most dramatic of which was the transcription factor ATFx (see Mishizawa et al., 1992, FEBS Lett. 299:36-38).

TABLE 1

Genes Transcriptionally Activated or Repressed Following IL-3 Withdrawal from FL5.12 Cells

| Gene (accession number) | Fold Change |
|---|---|
| 24p3 (X81627) | +12.6 |
| α-globin (L75940) | +12.3 |
| Leukocystatin (AF031825) | +7.7 |
| P40 phox (U59488) | +7.2 |
| E1B interacting protein (AF041054) | +7 |
| Erythroid Krueppel-like (M97200) | +6.5 |
| ATFx (AB012276) | −50.5 |

Northern blot analysis confirmed that IL-3 withdrawal resulted in transcriptional activation of 24p3 and repression of ATFx, consistent with the DNA microarray analysis. A time course experiment revealed that 24p3 transcriptional induction was first detectable within two hours following IL-3 withdrawal. Finally, we tested whether transcriptional activation of 24p3 following cytokine deprivation was specific to FL5.12 cells. We found that following IL-3 withdrawal, 24p3 transcription was also activated in 32D cells, another well-characterized IL-3 dependent cell line (See Greenberger et al., *Proc. Natl. Acad. Sci. USA* 80:2931-2935).

Example 3

24p3 Induces Apoptosis

Figure 2:
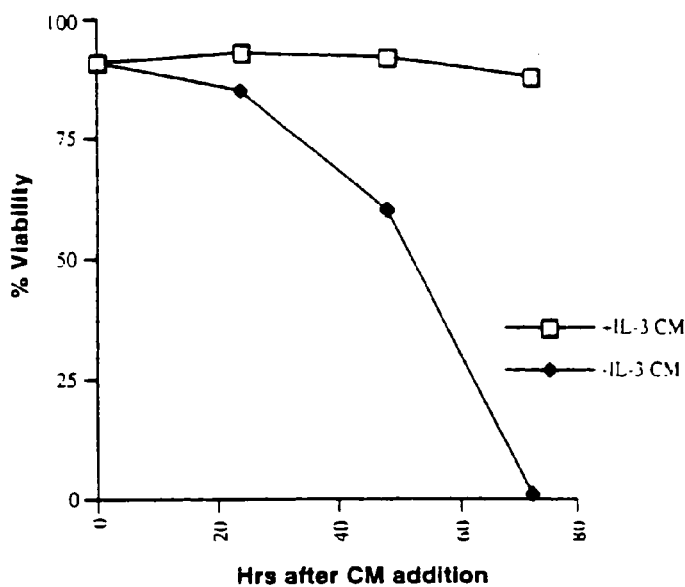
FIG. 2 is graph summarizing data from experiments wherein naive FL5.12 cells were exposed to culture medium from FL5.12 cells cultured in the presence or absence of IL-3. The results demonstrate that culture medium from IL-3-deprived FL5.12 cells induces apoptosis in naive FL5.12 cells. Cell viability was quantitated by trypan blue exclusion. "CM" designates culture medium. Open squares, CM supplemented with 3 ng/ml IL-3; closed diamonds, CM without IL-3 added.

In immunoblot experiments we found that following IL-3 withdrawal, 24p3 was in the culture medium of FL5.12 cells. We tested whether the culture medium from IL-3-deprived cells could induce apoptosis. Medium from cells cultured either in the presence or absence of IL-3 was collected, supplemented with recombinant IL-3, added to naive FL5.12 cells, and cell viability analyzed by a trypan blue vital dye exclusion assay. Experimental results summarized in FIG. 2 show that the medium from FL5.12 cells cultured in the absence IL-3 induced death of other FL5.12 cells even though IL-3 was present. In contrast, the medium from FL5.12 cells cultured in the presence of IL-3 had no effect (FIG. 2).

Experiments were performed to confirm that the cell death was apoptotic. Cells treated with the culture medium from IL-3-deprived cells and stained with annexin-V FITC/propidium iodide (PI) had fragmented DNA characteristic of apoptosis. These experiments confirmed that the 24p3-containing medium from IL-3-deprived FL5.12 cells was inducing apoptosis.

Figure 3:
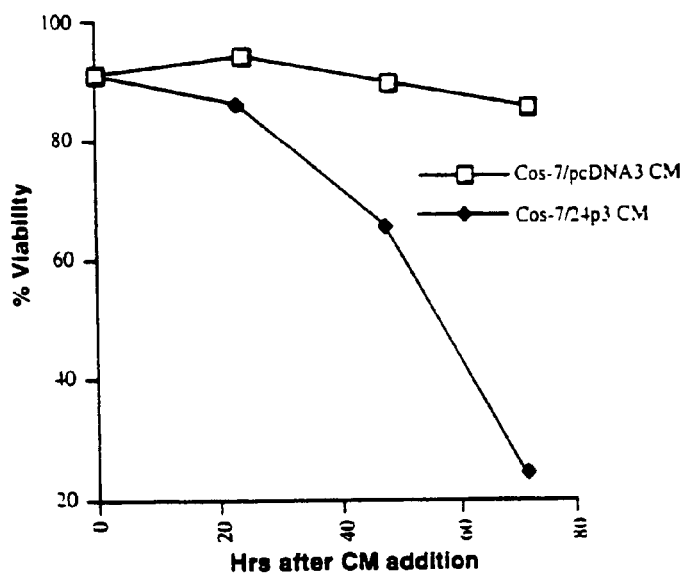
FIG. 3 is a graph summarizing data from experiments wherein naive FL5.12 cells were exposed to culture medium from COS-7 cells transfected with an expression vector containing a 24p3 coding sequence, or culture medium from COS-7 controls transfected with the expression vector only. The results demonstrate that the culture medium from COS-7 cells expressing 24p3 induce apoptosis. Open squares, medium from COS-7 cells expressing 24p3; closed diamonds, medium from COS-7 negative control cells.

Three experimental approaches were used to confirm that 24p3 in the culture medium was responsible for the induction of apoptosis. In the first approach, 24p3 was ectopically expressed in COS-7 cells (which are resistant to 24p3-mediated apoptosis). Expression and secretion of 24p3 was confirmed by Northern blot and immunoblot analyses. We found that the culture medium from COS-7 cells expressing 24p3 induced apoptosis in FL5.12 cells as evidenced by trypan blue exclusion (FIG. 3), Annexin-V FITC/PI staining and DNA fragmentation analysis. In contrast, culture medium from COS-7 cells transfected with only the expression vector (negative controls) displayed no apoptotic activity.

In the second approach, we tested whether ectopic expression of 24p3 in FL5.12 cells could induce apoptosis. A sequence encoding pre-24p3, i.e., with intact signal sequence, was placed under the control of an ecdysone-inducible promoter and stably introduced into FL5.12 cells. Addition of ecdysone induced expression and secretion of 24p3 and apoptosis. Comparable expression of a 24p3 derivative lacking the N-terminal signal sequence failed to induce cell death. This indicated that secretion of 24p3 is an essential step of this apoptotic pathway.

Figure 4:
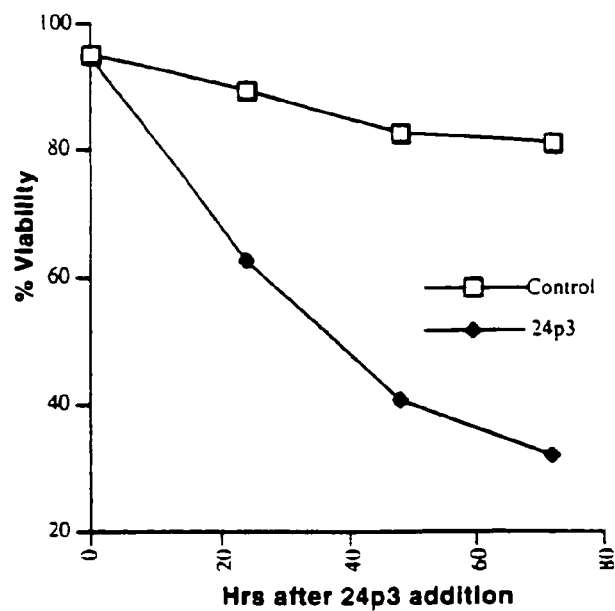
FIG. 4 is a graph summarizing data from experiments wherein the effect of purified 24p3 protein on cultured FL5.12 cells was tested. The results demonstrate that purified 24p3 protein induces apoptosis in FL5.12 cells. Viability was determined by trypan-blue exclusion at the indicated times. Open squares, negative control (no 24p3 protein added to medium); closed diamonds, purified 24p3 protein added to culture medium at a concentration of 10 ng/ml.

In the third approach, we tested whether direct addition of biochemically purified 24p3 polypeptide could induce apoptosis. We found that addition of purified mouse 24p3 (Chu et al., 1996, *Biochem. J.* 316:545-550) to FL5.12 cells led to apoptosis (FIG. 4). Collectively, these results indicated that when present in the culture medium, 24p3 promoted apoptosis of FL5.12 cells.

Example 4

Specificity

Several experiments were performed to assess the specificity of apoptosis promoted by 24p3 and transcriptional activation of the 24p3 gene. First, the cell type specificity of the 24p3 pro-apoptotic activity was examined (Table 2). Based upon trypan-blue exclusion and Annexin-V FITC/PI staining, 24p3 promoted apoptosis in a variety of (but not all) lymphoid cell lines, primary thymocytes, primary lymphocytes, and neutrophils. In contrast, non-lymphoid cells and monocyte-derived macrophages were resistant. Thus, the pro-apoptotic activity of 24p3 is highly cell type specific.

TABLE 2

Cell Type Specificity of 24p3-Mediated Apoptosis

| Cell type | Susceptibility to 24p3 |
|---|---|
| Lymphoid cell lines | |
| Cytokine-dependent | |
| IL-3 | |
| FL5.12 | Yes |
| FL5.12/Bcl-$x_L$ | No |
| 32D | Yes |
| BaF/3 | Yes |
| LyD9 | Yes |
| IL-2 | |
| HT-2 | Yes |
| IL-7 | |
| D1-F4 | Yes |
| Cytokine-independent | |
| Jurkat | No |
| MT-4 | Yes |
| WEHI 7.1.C.4 | Yes |
| Non-lymphoid cell lines | |
| HeLa | No |
| COS-7 | No |
| NIH 3T3 | No |
| U20S | No |
| Primary cells | |
| Murine primary Thymocytes | Yes |
| Murine primary Splenocytes | Yes |
| Human primary Neutrophils | Yes |
| Human primary Macrophages | No |
| Human peripheral blood lymphocytes | Yes |

Figure 5:
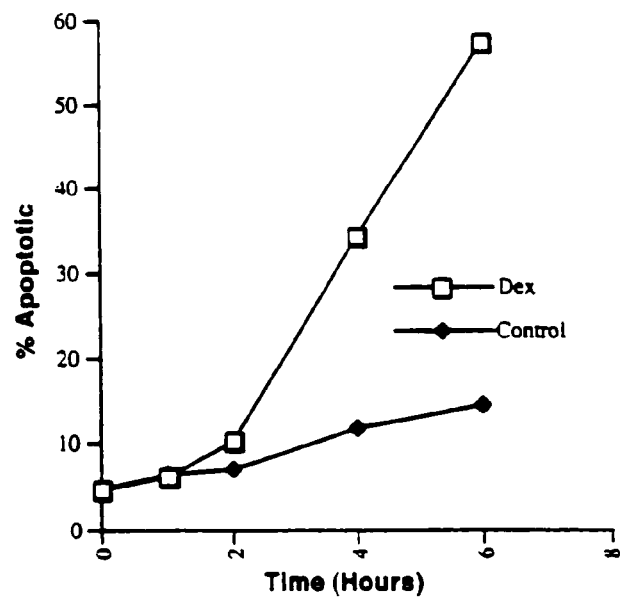
FIG. 5 is a graph summarizing data from experiments on the time course of cell death following dexamethasone addition to medium. Apoptosis was quantitated by Annexin V-FITC/PI staining. Open squares, dexamethasone treatment; closed diamonds, negative control.

Experiments were performed to assess the specificity of 24p3 transcriptional activation. Primary thymocytes are known to be highly prone to apoptosis, which can be efficiently promoted by a variety of agents, including 24p3 (Table 2) and corticosteroids (see Wyllie, 1980, *Nature* 284:555-556). The 24p3 promoter was known to have a glucocorticoid-response element (GRE) (See Garay et al., 1996, Gene 170:173-180). Therefore, the ability of 24p3 to be transcriptionally activated in primary thymocytes by the synthetic glucocorticoid, dexamethasone was tested. Northern blot analysis indicated that untreated primary thymocytes had a low level of 24p3 transcription, perhaps explaining their low spontaneous level of apoptosis. Significantly, addition of dexamethasone substantially increased 24p3 transcription and induced apoptosis with similar kinetics (FIG. 5). Taken together, these observations suggested a mechanism by which glucocorticoids induce apoptosis in primary thymocytes.

Figure 6:
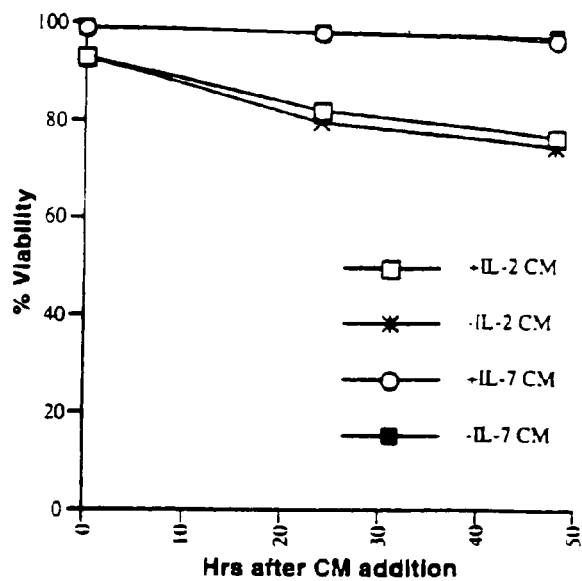
FIG. 6 is a graph summarizing results of experiments to test the ability of culture medium from cytokine-deprived IL-2 and IL-7-dependent cell lines to induce apoptosis. The results demonstrate that culture media from the cytokine-deprived IL-2 and IL-7-dependent cell lines are unable to induce apoptosis. Cell viability was quantitated by trypan blue exclusion. Open squares, culture medium from cells grown in presence of IL-2 added; stars, culture medium from cells grown in absence of IL-2 added; open circles, culture medium from cells grown in presence of IL-7 added; closed squares, culture medium from cells grown in absence of IL-7 added.

Transcriptional activation of 24p3 by cytokine withdrawal in cells dependent upon cytokines other than IL-3, transcription was tested. The IL-2 dependent cell line, HT-2 (see Watson, 1980, *J. Exp. Med.* 150:1510-1519), and the IL-7 dependent cell line, D1-F4 (see Khaled et al., 1999, *Proc. Natl. Acad. Sci. USA* 96:14476-14481) were analyzed (FIG. 6). Like FL5.12 cells, these cell lines were dependent on their respective cytokines for growth and undergo apoptosis upon cytokine withdrawal. It was found that 24p3 transcription was not activated in HT-2 cells grown in the absence of IL-2 or in D1-F4 cells grown in the absence of IL-7. Likewise, the medium from these cells cultured in the absence of cytokine did not induce apoptosis.

A variety of mammalian cell lines were known to undergo apoptosis when deprived of serum, similar to apoptosis in cytokine-dependent cell lines following cytokine withdrawal (See Barroso et al., 1997, *J. Bioenerg. Biomembr.* 29:259-267; and Pandey et al., 1994, *J. Cell Biochem.* 58:135-150). It was found that 24p3 transcription was not activated following withdrawal of serum from HL-60, Jurkat, or NIH 3T3 cells even though apoptosis occurred. Collectively, our results indicated that transcriptional activation of 24p3 following growth factor withdrawal was highly specific.

Example 5

IGF-1 Blocks 24p3 Transcriptional Activation

Figure 7:
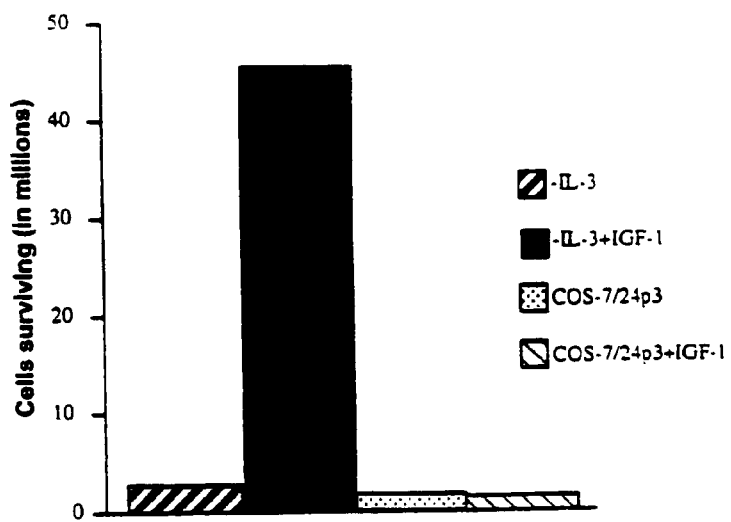
FIG. 7 is a histogram summarizing results from experiments to test the effect of IGF-1 on 24p3-mediated apoptosis. The results demonstrate that IGF-1 blocks apoptosis initiated by withdrawal of IL-3 from FL5.12 cells. The results also demonstrate that IGF-1 has no effect on apoptosis resulting from direct addition of 24p3 protein to the culture medium of FL5.12 cells. IGF-1 (Calbiochem) was added to IL-3 deprived or 24p3-treated FL5.12 cells (final concentration, 250 ng/ml) and cells analyzed for viability by trypan-blue exclusion at 48 hours.

Insulin-like growth factor-1 (IGF-1) stimulates proliferation and differentiation of a variety of cell types and can inhibit apoptosis resulting from deprivation of serum or cytokines (See Rodriguez-Tarduchy et al., 1992, *J. Immunol.* 149:535-540). These observations prompted us to investigate the effect of IGF-1 on 24p3-mediated apoptosis. As expected, IGF-1 blocked apoptosis initiated by withdrawal of IL-3 from FL5.12 cells. Unexpectedly, however, IGF-1 had no effect on apoptosis resulting from direct addition of 24p3 to FL5.12 cells (FIG. 7).

To investigate this observation, transcription of 24p3 under these different conditions was analyzed. Northern blot analysis revealed that IGF-1 blocked the transcriptional activation of 24p3 that normally occurred following IL-3 withdrawal. These results indicated that IGF-1 promoted survival following IL-3 withdrawal by inhibiting 24p3 transcriptional activation. Direct addition of 24p3 bypasses this transcriptional block, and therefore IGF-1 had no effect.

Example 6

Role of Bcl-2 Family Members

Previous studies have shown that several apoptotic pathways function by regulating phosphorylation of Bad, a pro-apoptotic member of the Bcl-2 family (see, e.g., Zha et al., 1996, *Cell* 87:619-628; and Datta et al., 1997, *Cell* 91-231-241). Phosphorylation of Bad blocks its pro-apoptotic activity, which is promoted by IL-3 through a pathway involving PI3K and Akt. Therefore, IL-3 deprivation results in dephosphorylation of Bad and apoptosis.

The finding that 24p3 induced apoptosis even when IL-3 was present, prompted us to analyze the effect of 24p3 on Bad phosphorylation. It was found that Bad was phosphorylated when cells were cultured in the presence of IL-3 and unphosphorylated following IL-3 withdrawal. Significantly, addition of 24p3 also led to dephosphorylation of Bad even though IL-3 was present. Thus, 24p3 appeared to be overriding the normal IL-3 signaling pathway leading to dephosphorylation of Bad and apoptosis.

Figure 8:
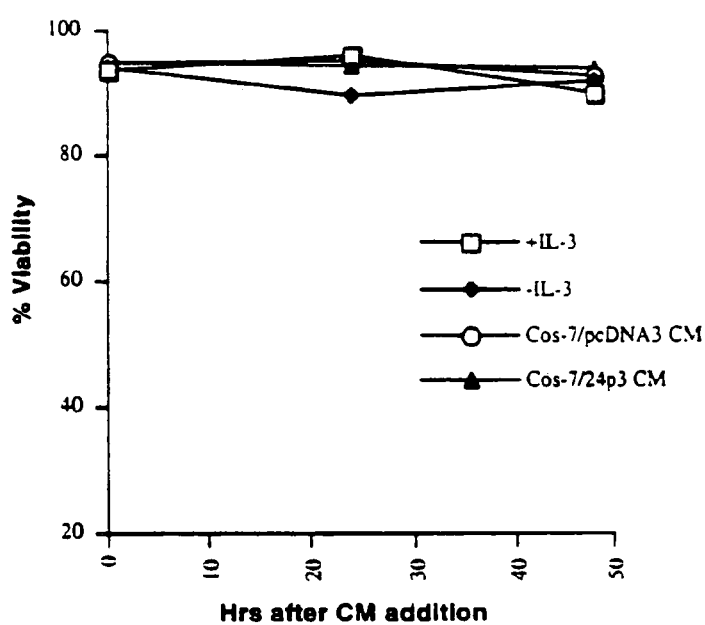
FIG. 8 is a graph summarizing results of experiments on the effect of Bcl-$X_L$ expression. The results demonstrate that both IL-3 withdrawal and 24p3 addition fail to induce cell death in FL5.12 cells expressing Bcl-$X_L$. Cell viability was quantitated by trypan-blue exclusion. Open squares, IL-3 present in medium; closed diamonds, IL-3 absent from medium; open circles, culture medium from 24p3 protein-expressing COS-7 cells added; closed triangles, culture medium from COS-7 control cells added.

The Bcl-2 family member, Bcl-$X_L$, was known to inhibit apoptosis induced by a variety of stimuli including IL-3 withdrawal (see Boise et al., 1993, *Cell* 74:597-608; Vanderheider et al., *Mol. Cell* 3:159-167). The activity of 24p3 in FL5.12 cells expressing Bcl-$X_L$ (FL5.12/Bcl-$X_L$ cells) was analyzed (FIG. 8). Culture media from IL-3 deprived FL5.12 cells and COS-7 cells expressing 24p3 failed to induce apoptosis of FL5.12/Bcl-$X_L$ cells. Thus, Bcl-$X_L$ blocked apoptosis induced both by IL-3 withdrawal and by 24p3 addition.

Apoptosis following 24p3 addition occurred more slowly than apoptosis resulting from IL-3 withdrawal. One explanation for this observation is that factors in addition to 24p3 may contribute to the efficiency of apoptosis following IL-3 withdrawal. In this regard, mNip3 and p40Phox, which have been previously implicated in apoptosis (See Chen et al., 1999, *J. Biol. Chem.* 274:7-10; Endres et al., 1997, *Immunity* 7:419-431), were also transcriptionally activated (Table 1). The reduced rate of apoptosis following 24p3 addition probably also reflects the fact that in these experiments the culture medium still contained IL-3, which promotes proliferation and survival.

IL-3 promotes cell survival through a signal transduction pathway involving PI3K and Akt[2,14] and resulting in an inactivating phosphorylation of the pro-apoptotic Bcl-2 family member, Bad. 24p3 is secreted and induces apoptosis upon addition to cells. It therefore seems likely that 24p3 functions through an extracellular receptor and initiates a signal transduction pathway. Addition of 24p3 also led to dephosphorylation of Bad even in the presence of IL-3. Thus, Bad may be the ultimate target of the 24p3 signal transduction pathway. 24p3 could act by blocking the PI3K/Akt pathway or in an independent pathway that promotes dephosphorylation of Bad.

These results indicate that 24p3 may be involved in immune system homeostasis, which requires that expanded cell populations be rapidly eliminated after their functions are completed. IL-3 is produced and secreted primarily by activated T cells and thus as the immune response begins to terminate IL-3 levels decrease. It has previously been recognized that declining IL-3 levels would prevent maturation of certain hematopoietic precursors and lead to apoptotic death of IL-3 dependent cells. The results presented herein reveal that declining IL-3 levels also induce 24p3 expression and secretion, providing an independent mechanism to facilitate termination of the immune response.

Example 7

Requirement of 24p3 Expression for Apoptosis Induced by IL-3 Deprivation

The requirement for 24p3 expression for apoptosis induced by IL-3 deprivation of FL5-12 cells was investigated using antisense experiments. Two phosphorothioate antisense (AS) oligonucleotides were used and a phosphorothioate sense oligonucleotide was used as a control.

The phosphorothioate oligonucleotides were purchased from Genosys (The Woodlands, Tex.). The sense and antisense 1 oligonucleotides spanned −12 to +5. Antisense 2 oligonucleotide spanned +585 to +593 of 24p3 mRNA (=1, translation start site). F15.12 cells were transfected with 2 µM of each oligonucleotide using Lipofectamine (Gibco-BRL). After 24 hours, cells were washed with RPMI medium plus 10% fetal calf serum (FCS) and again transfected with 2 μM of oligonucleotide. Cells were incubated for 24 hours after the second transfection then IL-3 was withdrawn.

Both 24p3 AS oligonucleotides substantially reduced 24p3 levels, whereas the sense oligonucleotide had no effect. The AS-1 nucleotide was particularly effective, preventing apoptosis in approximately 75% of the cells. Moreover, after treatment with 24p3 AS oligonucleotides, the conditioned medium from IL-3-deprived FL5.12 cells was no longer pro-apoptotic.

The ability of an antibody raised against 24p3 to block apoptosis was tested. In these experiments, 0.5 μg of affinity purified antibody against 24p3 (see Chu et al., *Biochem. J.* 316:545 (1996)) or 2 μg of preimmune serum was added after IL-3 withdrawal from IL-3 dependent primary bone marrow cells. Cell viability was then determined by annexin V-FITC/PI staining. Antibody against 24p3 blocked apoptosis in these cells, confirming that 24p3 is required to promote apoptosis.

The ability of 24p3 to promote apoptosis is cell type specific. Using trypan blue exclusion and annexin V-FITC/PI staining, 24p3 promoted apoptosis in many but not all leukocytic cell lines, primary thymocytes, primary lymphocytes, and neutrophils. In contrast, nonhematopoietic cells and monocyte-derived macrophages were resistant. These data demonstrate that 24p3-mediated apoptosis is cell type specific. Leukemias or other disorders characterized by the presence of cell types that are susceptible to 24p3/NGAL-induced apoptosis can be treated by administration of NGAL or NGAL-like polypeptides.

Other Embodiments

A number of embodiments of the invention have been described. Nevertheless, it will be understood that various modifications may be made without departing from the spirit and scope of the invention. For example, novel, human NGAL polypeptides occurring as a result of natural polymorphism may be found, and can be employed in the invention. Accordingly, other embodiments are within the scope of the following claims.

What is claimed is:

1. A method of inducing apoptosis in a lymphoid cell susceptible to NGAL-mediated apoptosis, the method comprising administering a polypeptide having at least 95% sequence identity to any one of SEQ ID NO: 5, SEQ ID NO: 6, or SEQ ID NO: 7 in an amount effective to induce apoptosis in the lymphoid cell, and wherein the polypeptide induces apoptosis in a lymphoid cell.

2. The method of claim 1, wherein the lymphoid cell is a mammalian cell.

3. The method of claim 1, wherein the polypeptide comprises a the amino acid sequence of SEQ ID NO:8.

4. The method of claim 1, wherein the polypeptide comprises an amino acid sequence selected from the group consisting of SEQ ID NO:5, SEQ ID NO:6, and SEQ ID NO:7.

5. The method of claim 1, wherein the polypeptide comprises the amino acid sequence of SEQ ID NO:5.

6. The method of claim 1, wherein the polypeptide comprises the amino acid sequence of SEQ ID NO:6.

7. The method of claim 1, wherein the polypeptide comprises the amino acid sequence of SEQ ID NO:7.

8. The method of claim 1, wherein the polypeptide comprises the amino acid sequence of SEQ ID NO:1.

9. The method of claim 1, wherein the polypeptide comprises the amino acid sequence of SEQ ID NO:2.

10. The method of claim 1, wherein the polypeptide comprises the amino acid sequence of SEQ ID NO:3.

* * * * *

SEQUENCE LISTING

```
<160> NUMBER OF SEQ ID NOS: 9

<210> SEQ ID NO 1
<211> LENGTH: 198
<212> TYPE: PRT
<213> ORGANISM: Homo sapiens

<400> SEQUENCE: 1

Met Pro Leu Gly Leu Leu Trp Leu Gly Leu Ala Leu Leu Gly Ala Leu
 1               5                  10                  15

His Ala Gln Ala Gln Asp Ser Thr Ser Asp Leu Ile Pro Ala Pro Pro
            20                  25                  30

Leu Ser Lys Val Pro Leu Gln Gln Asn Phe Gln Asp Asn Gln Phe Gln
        35                  40                  45

Gly Lys Trp Tyr Val Val Gly Leu Ala Gly Asn Ala Ile Leu Arg Glu
    50                  55                  60

Asp Lys Asp Pro Gln Lys Met Tyr Ala Thr Ile Tyr Glu Leu Lys Glu
65                  70                  75                  80

Asp Lys Ser Tyr Asn Val Thr Ser Val Leu Phe Arg Lys Lys Lys Cys
                85                  90                  95

Asp Tyr Trp Ile Arg Thr Phe Val Pro Gly Cys Gln Pro Gly Glu Phe
            100                 105                 110

Thr Leu Gly Asn Ile Lys Ser Tyr Pro Gly Leu Thr Ser Tyr Leu Val
        115                 120                 125

Arg Val Val Ser Thr Asn Tyr Asn Gln His Ala Met Val Phe Phe Lys
    130                 135                 140

Lys Val Ser Gln Asn Arg Glu Tyr Phe Lys Ile Thr Leu Tyr Gly Arg
145                 150                 155                 160

Thr Lys Glu Leu Thr Ser Glu Leu Lys Glu Asn Phe Ile Arg Phe Ser
                165                 170                 175

Lys Ser Leu Gly Leu Pro Glu Asn His Ile Val Phe Pro Val Pro Ile
            180                 185                 190

Asp Gln Cys Ile Asp Gly
        195
```

<210> SEQ ID NO 2
<211> LENGTH: 200
<212> TYPE: PRT
<213> ORGANISM: Mus musculus

<400> SEQUENCE: 2

Met Ala Leu Ser Val Met Cys Leu Gly Leu Ala Leu Leu Gly Val Leu
 1               5                  10                  15

Gln Ser Gln Ala Gln Asp Ser Thr Gln Asn Leu Ile Pro Ala Pro Ser
             20                  25                  30

Leu Leu Thr Val Pro Leu Gln Pro Asp Phe Arg Ser Asp Gln Phe Arg
         35                  40                  45

Gly Arg Trp Tyr Val Val Gly Leu Ala Gly Asn Ala Val Gln Lys Lys
     50                  55                  60

Thr Glu Gly Ser Phe Thr Met Tyr Ser Thr Ile Tyr Glu Leu Gln Glu
 65                  70                  75                  80

Asn Asn Ser Tyr Asn Val Thr Ser Ile Leu Val Arg Asp Gln Asp Gln
                 85                  90                  95

Gly Cys Arg Tyr Trp Ile Arg Thr Phe Val Pro Ser Ser Arg Ala Gly
            100                 105                 110

Gln Phe Thr Leu Gly Asn Met His Arg Tyr Pro Gln Val Gln Ser Tyr
        115                 120                 125

Asn Val Gln Val Ala Thr Thr Asp Tyr Asn Gln Phe Ala Met Val Phe
    130                 135                 140

Phe Arg Lys Thr Ser Glu Asn Lys Gln Tyr Phe Lys Ile Thr Leu Tyr
145                 150                 155                 160

Gly Arg Thr Lys Glu Leu Ser Pro Glu Leu Lys Glu Arg Phe Thr Arg
                165                 170                 175

Phe Ala Lys Ser Leu Gly Leu Lys Asp Asp Asn Ile Ile Phe Ser Val
            180                 185                 190

Pro Thr Asp Gln Cys Ile Asp Asn
        195                 200

<210> SEQ ID NO 3
<211> LENGTH: 198
<212> TYPE: PRT
<213> ORGANISM: Rattus rattus

<400> SEQUENCE: 3

Met Gly Leu Gly Val Leu Cys Leu Ala Leu Val Leu Gly Val Leu
 1               5                  10                  15

Gln Arg Gln Ala Gln Asp Ser Thr Gln Asn Leu Ile Pro Ala Pro Pro
             20                  25                  30

Leu Ile Ser Val Pro Leu Gln Pro Gly Phe Trp Thr Glu Arg Phe Gln
         35                  40                  45

Gly Arg Trp Phe Val Val Gly Leu Ala Ala Asn Ala Val Gln Lys Glu
     50                  55                  60

Arg Gln Ser Arg Phe Thr Met Tyr Ser Thr Ile Tyr Glu Leu Gln Glu
 65                  70                  75                  80

Asp Asn Ser Tyr Asn Val Thr Ser Ile Leu Val Arg Gly Gln Gly Cys
                 85                  90                  95

Arg Tyr Trp Ile Arg Thr Phe Val Pro Ser Ser Arg Pro Gly Gln Phe
            100                 105                 110

Thr Leu Gly Asn Ile His Ser Tyr Pro Gln Ile Gln Ser Tyr Asp Val
        115                 120                 125

Gln Val Ala Asp Thr Asp Tyr Asp Gln Phe Ala Met Val Phe Phe Gln

-continued

```
            130                 135                 140
Lys Thr Ser Glu Asn Lys Gln Tyr Phe Lys Val Thr Leu Tyr Gly Arg
145                 150                 155                 160

Thr Lys Gly Leu Ser Asp Glu Leu Lys Glu Arg Phe Val Ser Phe Ala
                165                 170                 175

Lys Ser Leu Gly Leu Lys Asp Asn Asn Ile Val Phe Ser Val Pro Thr
                180                 185                 190

Asp Gln Cys Ile Asp Asn
                195

<210> SEQ ID NO 4
<211> LENGTH: 200
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(200)
<223> OTHER INFORMATION: Xaa = Any Amino Acid

<400> SEQUENCE: 4

Met Xaa Leu Xaa Leu Leu Xaa Leu Gly Leu Ala Leu Leu Gly Xaa Leu
1               5                   10                  15

Xaa Xaa Gln Ala Gln Asp Ser Thr Xaa Xaa Leu Ile Pro Ala Pro Xaa
                20                  25                  30

Leu Xaa Xaa Val Pro Leu Gln Xaa Xaa Phe Xaa Xaa Xaa Gln Phe Xaa
            35                  40                  45

Gly Lys Trp Tyr Val Val Gly Leu Ala Gly Asn Ala Ile Xaa Arg Xaa
50                  55                  60

Xaa Xaa Xaa Xaa Xaa Xaa Met Tyr Xaa Thr Ile Tyr Glu Leu Xaa Glu
65                  70                  75                  80

Xaa Xaa Ser Tyr Asn Val Thr Ser Val Leu Xaa Arg Xaa Xaa Xaa Gln
                85                  90                  95

Gly Cys Xaa Tyr Trp Ile Arg Thr Phe Val Pro Xaa Xaa Xaa Xaa Gly
            100                 105                 110

Xaa Phe Thr Leu Gly Asn Ile Lys Xaa Tyr Pro Xaa Leu Xaa Ser Tyr
        115                 120                 125

Xaa Val Xaa Val Xaa Ser Thr Xaa Tyr Asn Gln Xaa Ala Met Val Phe
130                 135                 140

Phe Lys Lys Xaa Ser Xaa Asn Arg Xaa Tyr Phe Lys Ile Thr Leu Tyr
145                 150                 155                 160

Gly Arg Thr Lys Glu Leu Thr Xaa Glu Leu Lys Glu Xaa Phe Xaa Arg
                165                 170                 175

Phe Xaa Lys Ser Leu Gly Leu Xaa Glu Xaa Xaa Ile Val Phe Xaa Val
            180                 185                 190

Pro Xaa Asp Gln Cys Ile Asp Xaa
        195                 200

<210> SEQ ID NO 5
<211> LENGTH: 178
<212> TYPE: PRT
<213> ORGANISM: Homo sapiens

<400> SEQUENCE: 5

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe Gln Gly Lys Trp Tyr
```

```
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Cys Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
        115                 120                 125

Asn Arg Glu Tyr Phe Lys Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 6
<211> LENGTH: 180
<212> TYPE: PRT
<213> ORGANISM: Mus musculus

<400> SEQUENCE: 6

Gln Asp Ser Thr Gln Asn Leu Ile Pro Ala Pro Ser Leu Leu Thr Val
1               5                   10                  15

Pro Leu Gln Pro Asp Phe Arg Ser Asp Gln Phe Arg Gly Arg Trp Tyr
                20                  25                  30

Val Val Gly Leu Ala Gly Asn Ala Val Gln Lys Lys Thr Glu Gly Ser
        35                  40                  45

Phe Thr Met Tyr Ser Thr Ile Tyr Glu Leu Gln Glu Asn Asn Ser Tyr
    50                  55                  60

Asn Val Thr Ser Ile Leu Val Arg Asp Gln Asp Gln Gly Cys Arg Tyr
65                  70                  75                  80

Trp Ile Arg Thr Phe Val Pro Ser Ser Arg Ala Gly Gln Phe Thr Leu
                85                  90                  95

Gly Asn Met His Arg Tyr Pro Gln Val Gln Ser Tyr Asn Val Gln Val
            100                 105                 110

Ala Thr Thr Asp Tyr Asn Gln Phe Ala Met Val Phe Phe Arg Lys Thr
        115                 120                 125

Ser Glu Asn Lys Gln Tyr Phe Lys Ile Thr Leu Tyr Gly Arg Thr Lys
    130                 135                 140

Glu Leu Ser Pro Glu Leu Lys Glu Arg Phe Thr Arg Phe Ala Lys Ser
145                 150                 155                 160

Leu Gly Leu Lys Asp Asp Asn Ile Ile Phe Ser Val Pro Thr Asp Gln
                165                 170                 175

Cys Ile Asp Asn
            180

<210> SEQ ID NO 7
<211> LENGTH: 178
<212> TYPE: PRT
```

<213> ORGANISM: Rattus rattus

<400> SEQUENCE: 7

Gln Asp Ser Thr Gln Asn Leu Ile Pro Ala Pro Pro Leu Ile Ser Val
1               5                   10                  15

Pro Leu Gln Pro Gly Phe Trp Thr Glu Arg Phe Gln Gly Arg Trp Phe
            20                  25                  30

Val Val Gly Leu Ala Ala Asn Ala Val Gln Lys Glu Arg Gln Ser Arg
        35                  40                  45

Phe Thr Met Tyr Ser Thr Ile Tyr Glu Leu Gln Glu Asp Asn Ser Tyr
    50                  55                  60

Asn Val Thr Ser Ile Leu Val Arg Gly Gln Gly Cys Arg Tyr Trp Ile
65                  70                  75                  80

Arg Thr Phe Val Pro Ser Ser Arg Pro Gly Gln Phe Thr Leu Gly Asn
                85                  90                  95

Ile His Ser Tyr Pro Gln Ile Gln Ser Tyr Asp Val Gln Val Ala Asp
                100                 105                 110

Thr Asp Tyr Asp Gln Phe Ala Met Val Phe Phe Gln Lys Thr Ser Glu
            115                 120                 125

Asn Lys Gln Tyr Phe Lys Val Thr Leu Tyr Gly Arg Thr Lys Gly Leu
    130                 135                 140

Ser Asp Glu Leu Lys Glu Arg Phe Val Ser Phe Ala Lys Ser Leu Gly
145                 150                 155                 160

Leu Lys Asp Asn Asn Ile Val Phe Ser Val Pro Thr Asp Gln Cys Ile
                165                 170                 175

Asp Asn

<210> SEQ ID NO 8
<211> LENGTH: 200
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 2
<223> OTHER INFORMATION: Xaa = Pro or Ala
<220> FEATURE:
<221> NAME/KEY: VARIANT
<222> LOCATION: 4
<223> OTHER INFORMATION: Xaa = Gly or Ser
<220> FEATURE:
<221> NAME/KEY: VARIANT
<222> LOCATION: 5
<223> OTHER INFORMATION: Xaa = Leu or Val
<220> FEATURE:
<221> NAME/KEY: VARIANT
<222> LOCATION: 6
<223> OTHER INFORMATION: Xaa = Leu or Met
<220> FEATURE:
<221> NAME/KEY: VARIANT
<222> LOCATION: 7
<223> OTHER INFORMATION: Xaa = Trp or Cys
<220> FEATURE:
<221> NAME/KEY: VARIANT
<222> LOCATION: 15
<223> OTHER INFORMATION: Xaa = Ala or Val
<220> FEATURE:
<221> NAME/KEY: VARIANT
<222> LOCATION: 17
<223> OTHER INFORMATION: Xaa = His or Gln
<220> FEATURE:
<221> NAME/KEY: VARIANT
<222> LOCATION: 18
<223> OTHER INFORMATION: Xaa = Ala or Ser
<220> FEATURE:

```
<221> NAME/KEY: VARIANT
<222> LOCATION: 25
<223> OTHER INFORMATION: Xaa = Ser or Gln
<220> FEATURE:
<221> NAME/KEY: VARIANT
<222> LOCATION: 26
<223> OTHER INFORMATION: Xaa = Asp or Asn
<220> FEATURE:
<221> NAME/KEY: VARIANT
<222> LOCATION: 32
<223> OTHER INFORMATION: Xaa = Pro or Ser
<220> FEATURE:
<221> NAME/KEY: VARIANT
<222> LOCATION: 34
<223> OTHER INFORMATION: Xaa = Ser or Leu
<220> FEATURE:
<221> NAME/KEY: VARIANT
<222> LOCATION: 35
<223> OTHER INFORMATION: Xaa = Lys or Thr
<220> FEATURE:
<221> NAME/KEY: VARIANT
<222> LOCATION: 40
<223> OTHER INFORMATION: Xaa = Gln or Pro
<220> FEATURE:
<221> NAME/KEY: VARIANT
<222> LOCATION: 41
<223> OTHER INFORMATION: Xaa = Asn or Asp
<220> FEATURE:
<221> NAME/KEY: VARIANT
<222> LOCATION: 43
<223> OTHER INFORMATION: Xaa = Gln or Arg
<220> FEATURE:
<221> NAME/KEY: VARIANT
<222> LOCATION: 44
<223> OTHER INFORMATION: Xaa = Asp or Ser
<220> FEATURE:
<221> NAME/KEY: VARIANT
<222> LOCATION: 45
<223> OTHER INFORMATION: Xaa = Asn or Asp
<220> FEATURE:
<221> NAME/KEY: VARIANT
<222> LOCATION: 48
<223> OTHER INFORMATION: Xaa = Gln or Arg
<220> FEATURE:
<221> NAME/KEY: VARIANT
<222> LOCATION: 50, 146
<223> OTHER INFORMATION: Xaa = Lys or Arg
<220> FEATURE:
<221> NAME/KEY: VARIANT
<222> LOCATION: 61
<223> OTHER INFORMATION: Xaa = Ile or Val
<220> FEATURE:
<221> NAME/KEY: VARIANT
<222> LOCATION: 62
<223> OTHER INFORMATION: Xaa = Leu or Gln
<220> FEATURE:
<221> NAME/KEY: VARIANT
<222> LOCATION: 63, 152
<223> OTHER INFORMATION: Xaa = Arg or Lys
<220> FEATURE:
<221> NAME/KEY: VARIANT
<222> LOCATION: 64
<223> OTHER INFORMATION: Xaa = Glu or Lys
<220> FEATURE:
<221> NAME/KEY: VARIANT
<222> LOCATION: 65
<223> OTHER INFORMATION: Xaa = Asp or Thr
<220> FEATURE:
<221> NAME/KEY: VARIANT
<222> LOCATION: 66
<223> OTHER INFORMATION: Xaa = Lys or Glu
<220> FEATURE:
<221> NAME/KEY: VARIANT
<222> LOCATION: 67
<223> OTHER INFORMATION: Xaa = Asp or Gly
<220> FEATURE:
<221> NAME/KEY: VARIANT
<222> LOCATION: 68, 191
<223> OTHER INFORMATION: Xaa = Pro or Ser
```

-continued

```
<220> FEATURE:
<221> NAME/KEY: VARIANT
<222> LOCATION: 69
<223> OTHER INFORMATION: Xaa = Gln or Phe
<220> FEATURE:
<221> NAME/KEY: VARIANT
<222> LOCATION: 70
<223> OTHER INFORMATION: Xaa = Lys or Thr
<220> FEATURE:
<221> NAME/KEY: VARIANT
<222> LOCATION: 73
<223> OTHER INFORMATION: Xaa = Ala or Ser
<220> FEATURE:
<221> NAME/KEY: VARIANT
<222> LOCATION: 79
<223> OTHER INFORMATION: Xaa = Lys or Gln
<220> FEATURE:
<221> NAME/KEY: VARIANT
<222> LOCATION: 81
<223> OTHER INFORMATION: Xaa = Asp or Asn
<220> FEATURE:
<221> NAME/KEY: VARIANT
<222> LOCATION: 89, 189
<223> OTHER INFORMATION: Xaa = Val or Ile
<220> FEATURE:
<221> NAME/KEY: VARIANT
<222> LOCATION: 91
<223> OTHER INFORMATION: Xaa = Phe or Val
<220> FEATURE:
<221> NAME/KEY: VARIANT
<222> LOCATION: 93, 95
<223> OTHER INFORMATION: Xaa = Lys or Asp
<220> FEATURE:
<221> NAME/KEY: VARIANT
<222> LOCATION: 94
<223> OTHER INFORMATION: Xaa = Lys or Gln
<220> FEATURE:
<221> NAME/KEY: VARIANT
<222> LOCATION: 96
<223> OTHER INFORMATION: Xaa = Gln or absent
<220> FEATURE:
<221> NAME/KEY: VARIANT
<222> LOCATION: 97
<223> OTHER INFORMATION: Xaa = Gly or absent
<220> FEATURE:
<221> NAME/KEY: VARIANT
<222> LOCATION: 99
<223> OTHER INFORMATION: Xaa = Asp or Arg
<220> FEATURE:
<221> NAME/KEY: VARIANT
<222> LOCATION: 108
<223> OTHER INFORMATION: Xaa = Gly or Ser
<220> FEATURE:
<221> NAME/KEY: VARIANT
<222> LOCATION: 109
<223> OTHER INFORMATION: Xaa = Cys or Ser
<220> FEATURE:
<221> NAME/KEY: VARIANT
<222> LOCATION: 110
<223> OTHER INFORMATION: Xaa = Gln or Arg
<220> FEATURE:
<221> NAME/KEY: VARIANT
<222> LOCATION: 111
<223> OTHER INFORMATION: Xaa = Pro or Ala
<220> FEATURE:
<221> NAME/KEY: VARIANT
<222> LOCATION: 113, 153
<223> OTHER INFORMATION: Xaa = Glu or Gln
<220> FEATURE:
<221> NAME/KEY: VARIANT
<222> LOCATION: 119
<223> OTHER INFORMATION: Xaa = Ile or Met
<220> FEATURE:
<221> NAME/KEY: VARIANT
<222> LOCATION: 121
<223> OTHER INFORMATION: Xaa = Ser or Arg
<220> FEATURE:
<221> NAME/KEY: VARIANT
<222> LOCATION: 124
```

```
<223> OTHER INFORMATION: Xaa = Gly or Gln
<220> FEATURE:
<221> NAME/KEY: VARIANT
<222> LOCATION: 125
<223> OTHER INFORMATION: Xaa = Leu or Val
<220> FEATURE:
<221> NAME/KEY: VARIANT
<222> LOCATION: 126
<223> OTHER INFORMATION: Xaa = Thr or Gln
<220> FEATURE:
<221> NAME/KEY: VARIANT
<222> LOCATION: 129
<223> OTHER INFORMATION: Xaa = Leu or Asn
<220> FEATURE:
<221> NAME/KEY: VARIANT
<222> LOCATION: 131
<223> OTHER INFORMATION: Xaa = Arg or Gln
<220> FEATURE:
<221> NAME/KEY: VARIANT
<222> LOCATION: 133
<223> OTHER INFORMATION: Xaa = Val or Ala
<220> FEATURE:
<221> NAME/KEY: VARIANT
<222> LOCATION: 134
<223> OTHER INFORMATION: Xaa = Ser or Thr
<220> FEATURE:
<221> NAME/KEY: VARIANT
<222> LOCATION: 136, 186
<223> OTHER INFORMATION: Xaa = Asn or Asp
<220> FEATURE:
<221> NAME/KEY: VARIANT
<222> LOCATION: 148
<223> OTHER INFORMATION: Xaa = Val or Thr
<220> FEATURE:
<221> NAME/KEY: VARIANT
<222> LOCATION: 150
<223> OTHER INFORMATION: Xaa = Gln or Glu
<220> FEATURE:
<221> NAME/KEY: VARIANT
<222> LOCATION: 167
<223> OTHER INFORMATION: Xaa = Thr or Ser
<220> FEATURE:
<221> NAME/KEY: VARIANT
<222> LOCATION: 168
<223> OTHER INFORMATION: Xaa = Ser or Pro
<220> FEATURE:
<221> NAME/KEY: VARIANT
<222> LOCATION: 173
<223> OTHER INFORMATION: Xaa = Asn or Arg
<220> FEATURE:
<221> NAME/KEY: VARIANT
<222> LOCATION: 175, 194
<223> OTHER INFORMATION: Xaa = Ile or Thr
<220> FEATURE:
<221> NAME/KEY: VARIANT
<222> LOCATION: 178
<223> OTHER INFORMATION: Xaa = Ser or Ala
<220> FEATURE:
<221> NAME/KEY: VARIANT
<222> LOCATION: 184
<223> OTHER INFORMATION: Xaa = Pro or Lys
<220> FEATURE:
<221> NAME/KEY: VARIANT
<222> LOCATION: 185
<223> OTHER INFORMATION: Xaa = Glu or Asp
<220> FEATURE:
<221> NAME/KEY: VARIANT
<222> LOCATION: 187
<223> OTHER INFORMATION: Xaa = His or Asn
<220> FEATURE:
<221> NAME/KEY: VARIANT
<222> LOCATION: 200
<223> OTHER INFORMATION: Xaa = Gly or Asn

<400> SEQUENCE: 8

Met Xaa Leu Xaa Xaa Xaa Xaa Leu Gly Leu Ala Leu Leu Gly Xaa Leu
 1               5                  10                  15
```

```
Xaa Xaa Gln Ala Gln Asp Ser Thr Xaa Xaa Leu Ile Pro Ala Pro Xaa
        20                  25                  30

Leu Xaa Xaa Val Pro Leu Gln Xaa Xaa Phe Xaa Xaa Xaa Gln Phe Xaa
        35                  40                  45

Gly Xaa Trp Tyr Val Val Gly Leu Ala Gly Asn Ala Xaa Xaa Xaa Xaa
        50                  55                  60

Xaa Xaa Xaa Xaa Xaa Xaa Met Tyr Xaa Thr Ile Tyr Glu Leu Xaa Glu
65                  70                  75                  80

Xaa Xaa Ser Tyr Asn Val Thr Ser Xaa Leu Xaa Arg Xaa Xaa Xaa Xaa
            85                  90                  95

Xaa Cys Xaa Tyr Trp Ile Arg Thr Phe Val Pro Xaa Xaa Xaa Xaa Gly
            100                 105                 110

Xaa Phe Thr Leu Gly Asn Xaa Lys Xaa Tyr Pro Xaa Xaa Xaa Ser Tyr
            115                 120                 125

Xaa Val Xaa Val Xaa Xaa Thr Xaa Tyr Asn Gln Xaa Ala Met Val Phe
        130                 135                 140

Phe Xaa Lys Xaa Ser Xaa Asn Xaa Xaa Tyr Phe Lys Ile Thr Leu Tyr
145                 150                 155                 160

Gly Arg Thr Lys Glu Leu Thr Xaa Glu Leu Lys Glu Xaa Phe Xaa Arg
                165                 170                 175

Phe Xaa Lys Ser Leu Gly Leu Xaa Xaa Xaa Ile Xaa Phe Xaa Val
        180                 185                 190

Pro Xaa Asp Gln Cys Ile Asp Xaa
        195                 200

<210> SEQ ID NO 9
<211> LENGTH: 180
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 5
<223> OTHER INFORMATION: Xaa = Ser or Gln
<220> FEATURE:
<221> NAME/KEY: VARIANT
<222> LOCATION: 6, 61
<223> OTHER INFORMATION: Xaa = Asp or Asn
<220> FEATURE:
<221> NAME/KEY: VARIANT
<222> LOCATION: 12
<223> OTHER INFORMATION: Xaa = Pro or Ser
<220> FEATURE:
<221> NAME/KEY: VARIANT
<222> LOCATION: 14
<223> OTHER INFORMATION: Xaa = Ser, Leu or Ile
<220> FEATURE:
<221> NAME/KEY: VARIANT
<222> LOCATION: 15
<223> OTHER INFORMATION: Xaa = Lys, Thr or Ser
<220> FEATURE:
<221> NAME/KEY: VARIANT
<222> LOCATION: 20
<223> OTHER INFORMATION: Xaa = Gln or Pro
<220> FEATURE:
<221> NAME/KEY: VARIANT
<222> LOCATION: 21
<223> OTHER INFORMATION: Xaa = Asn, Asp or Gly
<220> FEATURE:
<221> NAME/KEY: VARIANT
<222> LOCATION: 23
<223> OTHER INFORMATION: Xaa = Gln, Arg or Trp
<220> FEATURE:
<221> NAME/KEY: VARIANT
<222> LOCATION: 24
<223> OTHER INFORMATION: Xaa = Asp, Ser or Thr
```

```
-continued

<220> FEATURE:
<221> NAME/KEY: VARIANT
<222> LOCATION: 25
<223> OTHER INFORMATION: Xaa = Asn, Asp or Glu
<220> FEATURE:
<221> NAME/KEY: VARIANT
<222> LOCATION: 26, 28
<223> OTHER INFORMATION: Xaa = Gln or Arg
<220> FEATURE:
<221> NAME/KEY: VARIANT
<222> LOCATION: 30
<223> OTHER INFORMATION: Xaa = Lys or Arg
<220> FEATURE:
<221> NAME/KEY: VARIANT
<222> LOCATION: 32
<223> OTHER INFORMATION: Xaa = Tyr or Phe
<220> FEATURE:
<221> NAME/KEY: VARIANT
<222> LOCATION: 38
<223> OTHER INFORMATION: Xaa = Gly or Ala
<220> FEATURE:
<221> NAME/KEY: VARIANT
<222> LOCATION: 41
<223> OTHER INFORMATION: Xaa = Ile or Val
<220> FEATURE:
<221> NAME/KEY: VARIANT
<222> LOCATION: 42
<223> OTHER INFORMATION: Xaa = Leu or Gln
<220> FEATURE:
<221> NAME/KEY: VARIANT
<222> LOCATION: 43
<223> OTHER INFORMATION: Xaa = Arg or Lys
<220> FEATURE:
<221> NAME/KEY: VARIANT
<222> LOCATION: 44
<223> OTHER INFORMATION: Xaa = Glu or Lys
<220> FEATURE:
<221> NAME/KEY: VARIANT
<222> LOCATION: 45
<223> OTHER INFORMATION: Xaa = Asp, Thr or Arg
<220> FEATURE:
<221> NAME/KEY: VARIANT
<222> LOCATION: 46
<223> OTHER INFORMATION: Xaa = Lys, Glu or Gln
<220> FEATURE:
<221> NAME/KEY: VARIANT
<222> LOCATION: 47
<223> OTHER INFORMATION: Xaa = Asp, Gly or Ser
<220> FEATURE:
<221> NAME/KEY: VARIANT
<222> LOCATION: 48
<223> OTHER INFORMATION: Xaa = Pro, Ser or Arg
<220> FEATURE:
<221> NAME/KEY: VARIANT
<222> LOCATION: 49
<223> OTHER INFORMATION: Xaa = Gln or Phe
<220> FEATURE:
<221> NAME/KEY: VARIANT
<222> LOCATION: 50
<223> OTHER INFORMATION: Xaa = Lys or Thr
<220> FEATURE:
<221> NAME/KEY: VARIANT
<222> LOCATION: 53
<223> OTHER INFORMATION: Xaa = Ala or Ser
<220> FEATURE:
<221> NAME/KEY: VARIANT
<222> LOCATION: 59
<223> OTHER INFORMATION: Xaa = Lys or Gln
<220> FEATURE:
<221> NAME/KEY: VARIANT
<222> LOCATION: 62
<223> OTHER INFORMATION: Xaa = Lys or Asn
<220> FEATURE:
<221> NAME/KEY: VARIANT
<222> LOCATION: 69
<223> OTHER INFORMATION: Xaa = Val or Ile
<220> FEATURE:
<221> NAME/KEY: VARIANT
<222> LOCATION: 71
```

```
<223> OTHER INFORMATION: Xaa = Phe or Val
<220> FEATURE:
<221> NAME/KEY: VARIANT
<222> LOCATION: 73
<223> OTHER INFORMATION: Xaa = Lys Asp or Gly
<220> FEATURE:
<221> NAME/KEY: VARIANT
<222> LOCATION: 74
<223> OTHER INFORMATION: Xaa = Lys or Gln
<220> FEATURE:
<221> NAME/KEY: VARIANT
<222> LOCATION: 75
<223> OTHER INFORMATION: Xaa = Asp or absent
<220> FEATURE:
<221> NAME/KEY: VARIANT
<222> LOCATION: 76
<223> OTHER INFORMATION: Xaa = Gln or absent
<220> FEATURE:
<221> NAME/KEY: VARIANT
<222> LOCATION: 77
<223> OTHER INFORMATION: Xaa = Lys or Gly
<220> FEATURE:
<221> NAME/KEY: VARIANT
<222> LOCATION: 79
<223> OTHER INFORMATION: Xaa = Asp or Arg
<220> FEATURE:
<221> NAME/KEY: VARIANT
<222> LOCATION: 88
<223> OTHER INFORMATION: Xaa = Gly or Ser
<220> FEATURE:
<221> NAME/KEY: VARIANT
<222> LOCATION: 89
<223> OTHER INFORMATION: Xaa = Cys or Ser
<220> FEATURE:
<221> NAME/KEY: VARIANT
<222> LOCATION: 90
<223> OTHER INFORMATION: Xaa = Gln or Arg
<220> FEATURE:
<221> NAME/KEY: VARIANT
<222> LOCATION: 91
<223> OTHER INFORMATION: Xaa = Pro or Ala
<220> FEATURE:
<221> NAME/KEY: VARIANT
<222> LOCATION: 93
<223> OTHER INFORMATION: Xaa = Glu or Gln
<220> FEATURE:
<221> NAME/KEY: VARIANT
<222> LOCATION: 99
<223> OTHER INFORMATION: Xaa = Ile or Met
<220> FEATURE:
<221> NAME/KEY: VARIANT
<222> LOCATION: 100
<223> OTHER INFORMATION: Xaa = Lys or His
<220> FEATURE:
<221> NAME/KEY: VARIANT
<222> LOCATION: 101
<223> OTHER INFORMATION: Xaa = Ser or Arg
<220> FEATURE:
<221> NAME/KEY: VARIANT
<222> LOCATION: 104
<223> OTHER INFORMATION: Xaa = Gly or Gln
<220> FEATURE:
<221> NAME/KEY: VARIANT
<222> LOCATION: 105
<223> OTHER INFORMATION: Xaa = Leu, Val or Ile
<220> FEATURE:
<221> NAME/KEY: VARIANT
<222> LOCATION: 106
<223> OTHER INFORMATION: Xaa = Thr or Gln
<220> FEATURE:
<221> NAME/KEY: VARIANT
<222> LOCATION: 109
<223> OTHER INFORMATION: Xaa = Leu, Asn or Asp
<220> FEATURE:
<221> NAME/KEY: VARIANT
<222> LOCATION: 111
<223> OTHER INFORMATION: Xaa = Arg or Gln
<220> FEATURE:
<221> NAME/KEY: VARIANT
```

```
<222> LOCATION: 113
<223> OTHER INFORMATION: Xaa = Val or Ala
<220> FEATURE:
<221> NAME/KEY: VARIANT
<222> LOCATION: 114
<223> OTHER INFORMATION: Xaa = Ser, Thr or Asp
<220> FEATURE:
<221> NAME/KEY: VARIANT
<222> LOCATION: 116, 118,166
<223> OTHER INFORMATION: Xaa = Asn or Asp
<220> FEATURE:
<221> NAME/KEY: VARIANT
<222> LOCATION: 120
<223> OTHER INFORMATION: Xaa = His or Phe
<220> FEATURE:
<221> NAME/KEY: VARIANT
<222> LOCATION: 126
<223> OTHER INFORMATION: Xaa = Lys, Arg or Gln
<220> FEATURE:
<221> NAME/KEY: VARIANT
<222> LOCATION: 128
<223> OTHER INFORMATION: Xaa = Val or Thr
<220> FEATURE:
<221> NAME/KEY: VARIANT
<222> LOCATION: 130
<223> OTHER INFORMATION: Xaa = Gln or Glu
<220> FEATURE:
<221> NAME/KEY: VARIANT
<222> LOCATION: 132
<223> OTHER INFORMATION: Xaa = Arg or Lys
<220> FEATURE:
<221> NAME/KEY: VARIANT
<222> LOCATION: 133
<223> OTHER INFORMATION: Xaa = Glu or Gln
<220> FEATURE:
<221> NAME/KEY: VARIANT
<222> LOCATION: 137
<223> OTHER INFORMATION: Xaa = Ile or Val
<220> FEATURE:
<221> NAME/KEY: VARIANT
<222> LOCATION: 145
<223> OTHER INFORMATION: Xaa = Glu or Gly
<220> FEATURE:
<221> NAME/KEY: VARIANT
<222> LOCATION: 147
<223> OTHER INFORMATION: Xaa = Thr or Ser
<220> FEATURE:
<221> NAME/KEY: VARIANT
<222> LOCATION: 148
<223> OTHER INFORMATION: Xaa = Ser, Pro or Asp
<220> FEATURE:
<221> NAME/KEY: VARIANT
<222> LOCATION: 153
<223> OTHER INFORMATION: Xaa = Asn or Arg
<220> FEATURE:
<221> NAME/KEY: VARIANT
<222> LOCATION: 155
<223> OTHER INFORMATION: Xaa = Ile, Thr or Val
<220> FEATURE:
<221> NAME/KEY: VARIANT
<222> LOCATION: 156
<223> OTHER INFORMATION: Xaa = Arg or Ser
<220> FEATURE:
<221> NAME/KEY: VARIANT
<222> LOCATION: 158
<223> OTHER INFORMATION: Xaa = Ser or Ala
<220> FEATURE:
<221> NAME/KEY: VARIANT
<222> LOCATION: 164
<223> OTHER INFORMATION: Xaa = Pro or Lys
<220> FEATURE:
<221> NAME/KEY: VARIANT
<222> LOCATION: 165
<223> OTHER INFORMATION: Xaa = Glu or Asp
<220> FEATURE:
<221> NAME/KEY: VARIANT
<222> LOCATION: 167
<223> OTHER INFORMATION: Xaa = His or Asn
<220> FEATURE:
```

```
<221> NAME/KEY: VARIANT
<222> LOCATION: 169
<223> OTHER INFORMATION: Xaa = Val or Ile
<220> FEATURE:
<221> NAME/KEY: VARIANT
<222> LOCATION: 171
<223> OTHER INFORMATION: Xaa = Pro or Ser
<220> FEATURE:
<221> NAME/KEY: VARIANT
<222> LOCATION: 174
<223> OTHER INFORMATION: Xaa = Ile or Thr
<220> FEATURE:
<221> NAME/KEY: VARIANT
<222> LOCATION: 180
<223> OTHER INFORMATION: Xaa = Gly or Asn

<400> SEQUENCE: 9

Gln Asp Ser Thr Xaa Xaa Leu Ile Pro Ala Pro Xaa Leu Xaa Xaa Val
 1               5                  10                  15

Pro Leu Gln Xaa Xaa Phe Xaa Xaa Xaa Xaa Phe Xaa Gly Xaa Trp Xaa
            20                  25                  30

Val Val Gly Leu Ala Xaa Asn Ala Xaa Xaa Xaa Xaa Xaa Xaa Xaa Xaa
            35                  40                  45

Xaa Xaa Met Tyr Xaa Thr Ile Tyr Glu Leu Xaa Glu Xaa Xaa Ser Tyr
    50                  55                  60

Asn Val Thr Ser Xaa Leu Xaa Arg Xaa Xaa Xaa Xaa Xaa Cys Xaa Tyr
65                  70                  75                  80

Trp Ile Arg Thr Phe Val Pro Xaa Xaa Xaa Xaa Gly Xaa Phe Thr Leu
                85                  90                  95

Gly Asn Xaa Xaa Xaa Tyr Pro Xaa Xaa Xaa Ser Tyr Xaa Val Xaa Val
            100                 105                 110

Xaa Xaa Thr Xaa Tyr Xaa Gln Xaa Ala Met Val Phe Phe Xaa Lys Xaa
            115                 120                 125

Ser Xaa Asn Xaa Xaa Tyr Phe Lys Xaa Thr Leu Tyr Gly Arg Thr Lys
    130                 135                 140

Xaa Leu Xaa Xaa Glu Leu Lys Glu Xaa Phe Xaa Xaa Phe Xaa Lys Ser
145                 150                 155                 160

Leu Gly Leu Xaa Xaa Xaa Ile Xaa Phe Xaa Val Pro Xaa Asp Gln
            165                 170                 175

Cys Ile Asp Xaa
            180
```